United States Patent [19]

Martin

[11] 4,141,718

[45] Feb. 27, 1979

[54] QUATERNARY AMMONIOALKANECARBOXYLIC ACID ANILIDES AS PLANT GROWTH INFLUENCING AGENTS

[75] Inventor: Henry Martin, Allschwil, Switzerland

[73] Assignee: Ciba-Geigy Corporation, Ardsley, N.Y.

[21] Appl. No.: 751,616

[22] Filed: Dec. 16, 1976

[30] Foreign Application Priority Data

Dec. 23, 1975 [CH] Switzerland ........................ 16704/75
Dec. 23, 1975 [CH] Switzerland ........................ 16705/75

[51] Int. Cl.[2] ........................ A01N 9/22; C07D 207/06

[52] U.S. Cl. ............................................ 71/95; 71/88; 71/90; 71/94; 71/118; 544/108; 260/239 BF; 260/307 R; 260/326.43; 260/562 N; 546/237; 546/337; 546/208; 546/226

[58] Field of Search ........................ 260/326.43; 71/95

[56] References Cited

U.S. PATENT DOCUMENTS 3,729,470 4/1973 Vaille ................................ 260/247.2
3,879,539 4/1975 Enders et al. ......................... 424/324
3,898,257 8/1975 Gregory ........................ 260/448.8 R

*Primary Examiner*—Raymond V. Rush
*Assistant Examiner*—Lisa Jones
*Attorney, Agent, or Firm*—Frederick H. Rabin

[57] ABSTRACT

This invention comprises new compounds and a composition for influencing, in particular for inhibiting, plant growth, which contains as active compound at least one quaternary ammonioalkancarboxylic acid anilide of the formula I

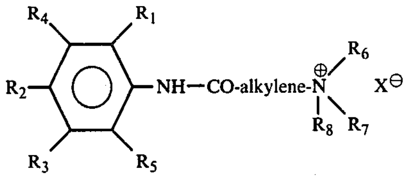

(I)

wherein each of $R_1$ to $R_5$ independently represents a hydrogen atom or any identical or different substituent, each of $R_6$ to $R_8$ independently represents an identical or different radical selected from the group consisting of alkyl, substituted alkyl, cycloalkyl, alkenyl, alkynyl, while two alkyl group together with the nitrogen atom can also form a saturated heterocyclic ring or three groups together can form an unsaturated heterocyclic ring a "alkylene" represents a saturated or unsaturated hydrocarbon bridge of 1 to 3 carbon atoms and X represents the anion of a non-phytotoxic acid HX.

Method for manufacturing these compounds are described and their use for inhibiting the growth of plants, in particular grass, cereals, soya, vegetables, fruit and ornamentals, for inhibiting the growth of side shoots in tobacco plants and for promoting the ripening and abscission of fruit.

42 Claims, No Drawings

QUATERNARY AMMONIOALKANECARBOXYLIC ACID ANILIDES AS PLANT GROWTH INFLUENCING AGENTS

The present invention provides compositions for regulating plant growth which contain as active components certain quaternary ammonioalkanoic acid anilides and a method of regulating plant growth which comprises the use of these active compounds and compositions which contain them. The invention also provides novel quaternay ammonioalkanoic acid arylides and a process for their manufacture.

A substantial number of quaternary aminoacetic anilides and pyridinioacetic anilides which possess pharmaceutical, disinfectant and bactericidal-fungicidal action etc. are known from the literature, but no particulars are provided relating to any positive and inhibiting action of these compounds with regard to plant growth. From the extensive literature, attention is drawn here only to a number of references, such as "Nature" 216, 1331-33 (1967), 223, 748 (1969); Europ. J. Pharmacology 13, 46 (1970); DOS No. 2,351,942; British patent specification No. 688,604; Journ. heterocycl. Chem., 8, 1079 (1971); Gazz. Chim. Ital. 95, 1237 (1965); Tetrahedron letters 1969, 4945 etc.

Certain quaternary aminoacetic anilides have already been suggested for different technical purposes, for example as moth repellents (U.S. Pat. No. 2,343,071 and German Reichspatent No. 905373 etc.).

None of these publications contains the remotest allusion to or indication of a plant growth-influencing action of such known compounds.

On the other hand, quaternary ammonium compounds having another structure are on the market as plant regulators and are described in detail for example in R. Wegler's "Chemie der Pflanzenschutz- und Schädlingsbekämpfungsmittel", vol. 2, Springer Verlag, 1970, pp. 323-326 and 407, with reference to the original literature.

Further quaternary ammonium compounds with a plant growth-regulating action have become known for example from Ann. Appl. Biol. 63, 211 (1969); from U.S. Pat. Nos. 3,701,799, 3,580,716, 3,856,850 and 3,895,933, and from the Journ. Agr. and Food Chem. 7, 264 (1959) and 16, 523 (1968). However, all these prior art growth-regulators are not quaternary ammonioalkanoic acid anilides, but are to some extent very complicated organic compounds.

The present invention is based on the surprising observation that quaternary ammonioalkanecarboxylic anilides of the formula I

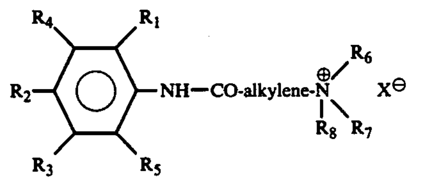

(I)

wherein each of $R_1$ to $R_5$ independently represents a hydrogen atom or any identical or different substituent, each of $R_6$ to $R_8$ independently represents an identical or different radical selected from the group consisting of alkyl, cycloalkyl, alkenyl, alkynyl, cyanoalkyl, halogenalkyl, hydroxyalkyl, aralkyl, amino, alkoxyalkyl or carbalkoxyalkyl, whilst two alkyl groups together with the nitrogen atom to which they are attached can also form a saturated heterocyclic ring which can contain in addition an oxygen atom as ring member, or three groups together can form an unsaturated heterocyclic ring which can contain a further nitrogen atom as ring member, "alkylene" represents a saturated or unsaturated straight-chain or branched hydrocarbon bridge containing not more than 3 carbon atoms, and X represents the anion of any non-phytotoxic acid HX, possess outstanding plant growth-regulating properties in mono-and especially dicotyledonous plants, and can be used for example as growth inhibitors for grasses, cereals, soya, beans, ornamentals, fruit etc., and some also have an abscission effect on fruit and leaves.

Preferred aliphatic open-chain radicals $R_6$ to $R_8$ are low molecular straight-chain or branched radicals containing not more than 6 carbon atoms. The alkylene chain is preferably represented by $-CH_2-$ (ammonioacetic acid anilides), but can also be

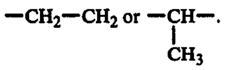

One of the open-chain radicals $R_6$ to $R_8$ can contain at least 3 carbon atoms, and two together can contain at least 4 carbon atoms.

In addition, those anilides are preferred which carry at least 1 to 5 substituents in the aniline nucleus. The substituents $R_1$ to $R_5$, one or more of which can be in any positions, include: alkyl (straight-chain and branched) containing not more than 4 carbon atoms, cycloalkyl, lower alkoxy, halogen (fluorine, chlorine, bromine), halogenalkyl, such as trifluoromethyl, halogenalkoxy, halogenalkylthio, hydroxyl, alkoxycarbonyl, alkenyl, alkenyloxy, alkynyloxy, alkylcarbonyl, such as acetyl, alkylthio, alkylsulphamoyloxy, nitro, alkylcarbonylamino, alkylcarbamoyl, cyano, alkylsulphonyl, piperidinocarboxy, pyrrolidinocarboxy, piperidinocarbonylamino, pyrrolidino-carbonylamino etc.

Particularly interesting novel active substances are those of the narrower formula 1a

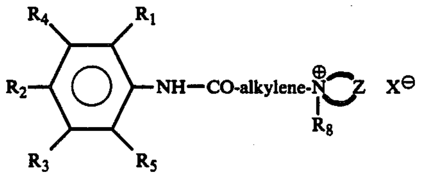

(Ia)

wherein $R_1$ to $R_5$, "alkylene" and X are as defined in formula I, $R_8$ represents a lower alkyl, cycloalkylalkyl, alkenyl, alkynyl, cyanoalkyl, halogenalkyl, hydroxyalkyl, alkoxyalkyl or carbalkoxyalkyl group and Z represents a 4- to 6-membered saturated hydrocarbon bridge, in which a bridge member can be replaced by an oxygen atom. The ring system formed by Z is preferably a pyrrolidine ring, and also piperidine and hexamethyleneimine.

Further preferred compounds from a biological point of view are those of the formula I in which $R_4$ and $R_5$ represent hydrogen atoms, namely those which carry a maximum of 3 substituents $R_1$, $R_2$ and $R_3$ in the 2,4- and 5-position of the anilide radical, whilst $R_1$ represents a hydrogen atom, a chlorine atom, a methyl or $CF_3$ group, $R_2$ represents a methyl group, a halogen atom or a lower alkoxy group, and $R_3$ represents a hydrogen atom, a chlorine atom, or a $CF_3$ group.

$R_6$ to $R_8$ are then preferably alkyl, cyanoalkyl, alkenyl or alkynyl groups, whilst two of these substituents together with the nitrogen atom to which they are attached can also form a saturated heterocyclic ring which can additionally contain an oxygen atom as ring member.

A substituent $R_2$ in 4-position (preferably chlorine) must therefore be present and $R_1$ in 2-position should preferably not be a hydrogen atom (2,4-substitution). $R_1$ and $R_2$ preferably represent methyl groups and chlorine atoms.

The most interesting novel compounds of this type are those of the narrower formula (Ib)

(Ib)

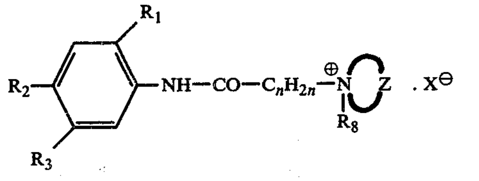

wherein $R_1$ to $R_3$ are as defined above, $n$ is 1 or 2 (preferably 1), $R_8$ represents a lower alkyl, alkenyl or alkynyl group and Z represents a 4- to 6-membered saturated, substituted or unsubstituted hydrocarbon bridge, in which a bridge member which is not adjacent to the nitrogen atom can be replaced by an oxygen atom. The pyrrolidine ring formed by Z is the preferred heterocyclic ring.

The anion X can be selected from any of the non-phytotoxic acids and has no appreciable influence on the biological action.

According to the present invention, novel compounds of the formula I, Ia and Ib are obtained by methods which are known per se by reacting an aniline of the formula II (II)

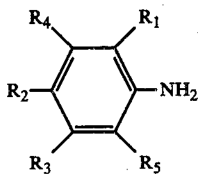

with a reactive haloalkanoic acid derivative to give a haloalkanecarboxylic acid anilide of the formula III (III)

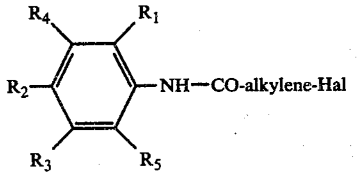

and then reacting this compound with ammonia or primary, secondary or tertiary aliphatic amines or aliphatic-alicyclic amines or with cyclic amines which contain a ring oxygen atom, or with an unsaturated cyclic amine, and converting the resultant amino-fatty acid anilides if necessary with a quaternising agent into the end products of the formulae Ia and Ib.

Suitable unsaturated cyclic amines are pyridine, pyrrole, pyrazole and alkylated derivatives thereof.

Preferred cyclic ammonio derivatives of the formulae Ia and Ib are obtained by using for the reaction with the compound of the formula III an aliphatic-cyclic amine which optionally contains a ring oxygen atom.

The intermediates of the formula III are obtained by treating an aniline of the formula II with halogen-substituted fatty acids or suitable derivatives, such as the esters, halides, amides or anhydrides thereof.

As examples of anilines of the formula II there may be mentioned: aniline, 2,4-dichloroaniline, 2,5-dichloroaniline, 3,4-dichloroaniline, 2,6-dichloroaniline, 2,4,5-trichloroaniline, 3-chloro-4-fluoro-aniline, 2methyl-4,5-dichloroaniline, 3-chloro-4-methylaniline, 2-chloro-4-methylaniline, 2-methyl-4-chloroaniline, 3-trifluoromethyl-4-chloro-aniline, 2,4-dimethylaniline, 3,4-dimethylaniline, p-toluidine, 4-chloroaniline, 3-chloroaniline, 2-methyl-4-bromoaniline, 2-chloro-4-bromoaniline, 2-trifluoromethyl-4-chloroaniline, 3-methylaniline, 2-(3)methyl-4-(piperidinocarboxy)-5(or -6)-isopropyl-aniline, 2-methyl-4-(pyrrolidinocarboxy)-5-tert.-butyl-aniline, 3-chloro-4-isopropyl-aniline, 3,5-bis-trifluoromethyl-aniline, 2,4,6-trimethylaniline, 2-methyl-6-chloroaniline, 2-methylaniline, 2-methoxy-aniline, 2-methoxy-5-chloroaniline, 3-methylthio-aniline, 3,5-dimethylaniline, 2,4,5-trimethylaniline, 2,3,5,6-tetramethylaniline, 3-methoxycarbonyl-4-hydroxy-aniline, 2-methyl-4-hydroxy-aniline, 4-n-butyloxy-aniline, 2-methyl-4-n-butyloxy-aniline, 2,6-dimethyl-4-n-butyloxy-aniline, 2,6-dimethyl-4-n-butyloxyaniline, 3-chloro-4-propoxy-aniline, 3,5-dichloro-4-methoxy-aniline, 3-chloro-4-ethoxyaniline, 2-methyl-6-ethoxyaniline, 2-methyl-6-ethoxycarbonyl-aniline, 2-chloro-6-methoxy-aniline, 2,6-dimethoxyaniline, 2,6-dichloro-4-methylaniline, 2-methyl-5-isopropylaniline, 2-fluoroaniline, 2,4-difluoroaniline, 2-fluoro-4-chloroaniline, 2,4-difluoro-5-chloroaniline, 3-chloro-4-allyloxy-aniline, 3,4,5-trichloro-aniline, 3,5-dichloro-4-methylaniline, 3-chloro-4-tert.-butyl-aniline, 2-, 3- or 4-ethylaniline, 3-chloro-4-ethyl-aniline, 3- or 4-acetylaniline, 4-vinylaniline, 4-α-methylvinyl-aniline, 2,4,6-tribromoaniline, 2,3- and 3,5-dichloroaniline, 2-methoxycarbonyl-aniline, 2- and 3-isopropoxycarbonyl-aniline, 2-chloro-3-methyl-aniline, 2-methyl-3-chloro-aniline, 2,3-di-methylaniline, 2,4-dimethoxy-4-chloro-aniline, 4-dimethylsulphamoyl-aniline, 2-methyl-4-nitro-5-chloro-aniline, pentamethylaniline, 2-methyl-4-methoxy-aniline, 2-methoxy-5-methyl-aniline, 1,2-diamino-4-chlorobenzyl, 2-methoxy-5-methylcarbonyl-amino-aniline, 2-ethoxy-aniline, 4-isopropylcarbamoyl-aniline, 2-fluoro-4,5-dichloro-aniline, 4-methoxycarbonyl-aniline, 2-hydroxy-3-methoxycarbonyl-aniline, 3,4-bis(trifluoromethyl)-aniline, 2-fluoro-5-trifluoromethyl-aniline, 3-tert.-butylcarbamoyl-aniline, 3-tert.-butyl-carbamoyl-4-chloro-aniline, 3-chloro-4-methylsulphonyloxy-aniline, 3- or 4-trifluoromethylthio-aniline, 4-methylsulphonyloxy-aniline, 3-dimethylsulphamoyloxy-aniline, 3-chloro-4-trifluoromethoxy-aniline, 2-fluoro-4-bromo-aniline, 4-cyclopropyl-aniline, 3-chloro-4-difluorochloromethoxy-aniline, 2- and 3-trifluoromethyl-aniline, N-acetyl-2,4-dichloroaniline, 2-pyrrolidinocarbamoylamino-aniline, 3-piperidinocarbamoylamino-aniline, 2,3,4-trichloroaniline, 2-ethyl-4- chloro-aniline, 2,5-dimethyl-4-bromo-aniline, 2-methyl-4,6-dibromoaniline, 2-methyl-4-bromo-6-chloro-aniline, 2,5-dimethyl-4-chloro-aniline, 2-methyl-4-bromo-5-chloro-aniline, 2,6-dimethyl-4-chloro-aniline, 2,4-dichloro-6-methylaniline etc.

Suitable halogen-substituted fatty acids and derivatives thereof are, for example, α-halogenoacetic acid, α-halogenopropionic acid, β-halogenopropionic acid and the monohalogeno-butyric acids and halogenocrotonic acids.

The reaction of the halogen-substituted fatty acid anilides of the formula III with amines is carried out by known methods to form — when ammonia or primary, secondary or tertiary amines are used, with attendant dehydrohalogenation — the corresponding primary to quaternary amino fatty acid anilides. Examples of such reactive amines are: ammonia, methylamine, ethylamine, propylamine, butylamine, dimethylamine, diethylamine, methylethylamine, dipropylamine, methylpropylamine, methylbutylamine, dibutylamine, hexylamine, allylamine, diallylamine, pyrrolidine, piperidine, 2,3- or 4-methylpiperidine, N-methylpiperidine, morpholine, 1-methylamino-1-methylpropine-2N-methyl-N-allylamine, N-methyl-N-methallylamine, propargylamine, cyanomethylamine, hexamethylenimine, trimethylamine, triethylamine, dimethylamino-acetonitrile, diethylaminoacetonitrile, tripropylamine, and many other such amines, such as N-alkyl-N-cyclopropylamethylamines, for example dimethylhydrazine etc.

If during the reaction of the halogen-substituted fatty acid amides with the above amines these amines are so chosen that primary, secondary or tertiary amino-fatty acid anilides are formed, then a subsequent aftertreatment is carried out until quaternary substitution of the nitrogen atom is effected. This aftertreatment is performed with the customary quaternising agents, for example with mineral acid esters of saturated or unsaturated alcohols, such as alkyl, alkenyl or alkinyl halides, dialkylsulphates, or by the addition of sulphonic acid esters and halogenocyanoalkanes. Suitable quaternising agents are all those which are capable of introducing the radicals $R_6$ to $R_8$, whereby this last mentioned radical is introduced by an aftertreatment.

Examples of quaternising agents are: chloromethyl, bromomethyl, iodomethyl, ethyl bromide, ethyl iodide, propyl chloride, propyl bromide, propyl iodide, butyl iodide, butyl bromide, allyl chloride, allyl bromide, propargyl bromide, crotyl bromide, chloroacetonitrile, bromoacetonitrile, alkyl bromoacetate, bromoacetic amide, benzyl chloride, iso-butyl iodide etc.

A modification of the process for obtaining the ammonium compounds of the formula (I) comprises the use of halogen-substituted fatty acid esters with reactive halogen, for example phenyl chloroacetate, as starting compounds, reacting these compounds with the cited amines and quaternising agents to give quaternary amino-fatty acid phenyl esters, and subsequently amidising these latter, for example in aqueous or aqueous-alcoholic solution or emulsion, with anilines of the formula II, with attendant exchange of the phenol, to give the claimed quaternary amino-fatty acid anilides of the formula (I).

A further modification of the process described herein for the manufacture of ammonioacetic acid anilides comprises reacting betaine dichlorides with the substituted anilines of the formula II.

The quaternary ammonium salts of the formula I possess the plant growth-regulating action, in particular a plant growth-retarding action.

Accordingly, compounds of the formula (I) can be used for controlling the growth of plants in agriculture and in horticulture. A variety of typical methods of application is listed hereinafter:

For reducing the labour and expense involved in cutting by inhibiting the herbaceous soil covering on road shoulders, canal embankments, in airports, fruit plantations, on turf for sporting activities and ornamental grass plots etc., and for inhibiting the growth of shoots of bushes, hedges, ornamental bushes, fruit and other trees.

For inhibiting unwanted suckers in tobacco plants and other cultures.

For increasing the yield in cultures of leguminosae (for example soya and ground nuts) by inhibiting the vegetative growth in favour of the generative growth.

For increasing the stability of crops of plants which are susceptible to lodging, such as cereals, maize and soya (preventing the plants from being flattened under unfavourable weather conditions).

For inhibiting the excessive growth of ornamentals which are reared in pots, such as chrysanthemums, poinsettia, etc.

For increasing the blossoming of cultivated plants, for example young fruit trees.

For speeding up the ripening of fruit.

For facilitating the harvesting of fruit by promoting the formation of separation tissue between the fruit and the shoots of the plants.

Many compounds also possess bactericidal and fungicidal properties.

The quaternary ammonium salts of the formula (I) are used in the form or preparations which, in addition to containing the quaternary ammonium salt of the formula (I), also contain a carrier or a surface-active agent or a carrier and a surface-active agent. The effectiveness of the quaternary ammonium salts of the formula (I) depends on the concentration when they are used as plant growth-regulators. In addition, substantial variations with regard to the active concentration of the quaternary ammonium salts of the formula (I) as plant growth-regulators are possible, this concentration being dependent not only on the species, organism or nature of the plants to be treated, but also on the physiological age of the plants. The concentration to be applied should therefore be selected depending on the composition employed, the species of plant, and the duration of the application. In general, effective concentrations are in the range between 1 and 5000 ppm and preferably between 10 and 500 ppm. However, these values are of no particular importance.

The active compounds of the formula (I) can be used by themselves or in combination with other regulators, with trace elements, chelates, fertilisers, and also with fungicides, insecticides and acaricides. Furthermore, stabilisers can also be added to the active compounds and the compositions which contain them.

From the point of view of effectiveness, all those active compounds of the formula I are suitable which are unsubstituted or monosubstituted to pentasubstituted in the aniline nucleus. The preferred nuclear substituents $R_1$ to $R_5$ are methyl, chlorine, fluorine and trifluoromethyl. Preferred substituents of monosubstituted compounds are p-chlorine and p-fluorine ($R_2$). The preferred disubstitution is the 2,4-, 3,4- and 2,5-position in the aniline ring, whilst the 2,6-position is also of interest. The preferred trisubstitution is the 2,4,5-position.

Particularly preferred radicals at the quaternary nitrogen atom, that is to say, especially for $R_8$, are propyl, allyl, propargyl, butyl and butenyl radicals in that order. Methyl and ethyl groups are also possible however. If $R_6$ and $R_7$ are also open-chain radicals, all the radicals $R_6$ to $R_8$ can be low molecular (containing 1 to 2 carbon atoms) in order to exhibit outstanding action.

The following Example illustrates the manufacture of active compounds containing to the invention of the formula Ia and Ib.

EXAMPLE 1

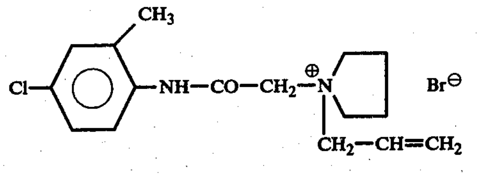

282 g of freshly distilled 2-methyl-4-chloroaniline (2 moles) are added to 500 ml of acetone and a solution of 246 g (3 moles) of anhydrous sodium acetate in 800 ml of water is added thereto. With virorous stirring, 190 ml of chloroacetyl chloride (2.5 moles) are added dropwise in the course of 3 hours while keeping the temperature at 35° to 55° C. by cooling with ice-water. When the addition is complete, stirring is continued for a further 2 hours at room temperature and thereafter 400 ml of ice-water are added. After the batch has cooled to 5° to 10° C., the chloroacetyl-2-methyl-4-chloroanilide is collected with suction, washed thoroughly with water and dried in vacuo at 60° C. Yield: 423 g = 97% of theory. Melting point: 128°-129° C. 21.8 g (0.1 mole) of chloroacetyl-2-methyl-4-chloroanilide are dissolved in 100 ml of absolute alcohol and stirred with 21.3 g (0.3 mole) of pyrrolidine and the temperature rises to boiling point. Stirring is subsequently continued for 3 hours at room temperature. The crude product is concentrated in vacuo, diluted with water, and the base extracted with ether. After it has been washed repeatedly with water, the ethereal extract is dried over $Na_2SO_4$ and concentrated. Yield: 46.4 g. After recrystallisation from hexane, the pyrrolidinoacetic acid-2-methyl-4-chloroanilide melts at 62°-64° C.

12.6 g of pyrrolidinoacetic acid 2-methyl-4-chloroanilide (0.05 mole) are dissolved in 50 ml of ethyl acetate and treated with 6 g of allyl bromide. The reaction mixture is refluxed for 4 hours and the quaternary compound initially separates out as an oil, which crystallises after a brief time. After filtration with suction, the precipitate is washed with ethyl acetate and the product dried in vacuo at 50° C. Yield: 18 g (= 96.8% of theory). The product melts at 145°-147° C. and dissolves in water to give a clear solution. (Compound 1).

Analysis: $C_{16}H_{22}ClN_2O$ . Br Mg 373.7

| | C | H | N | Cl | Br |
|---|---|---|---|---|---|
| Calculated | 51.4% | 5.9% | 7.5% | 9.5% | 21.38% |
| Found | 51.5% | 6.2% | 7.6% | 9.6% | 2.4% |

From this salt (bromide), two further salts of this compound are prepared as follows:

18.68 g of the bromide (compound 1) are dissolved hot in 350 ml of distilled water, filtered, and then a solution of 8.5 g of silver nitrate in 50 ml of water are added at room temperature with stirring. The reaction flask is protected from light with tin foil, heated for 15 minutes in a steam bath and allowed to stand for 5 hours. The batch is subsequently filtered, washed with water and the filtrate is evaporated in vacuo. The residual oil is triturated with ethyl acetate and congeals in the process. The solid residue is dried in vacuo at 45° C. to yield 15.5 g of nitrate ($X^{\ominus} = NO_3^{\ominus}$) with a melting point of 106°-108° C. (Compound 1*a*).

In like manner, the above bromide (compound 1) is converted with silver trifluoromethanesulphonate into the trifluoromethanesulphonate with a melting point of 89°-91° C. (compound 1*b*).

$(K^{\ominus} = F_3C-SO_3^{\ominus})$

The following compounds were obtained in corresponding manner:

| Example | | Melting point in ° C. |
|---|---|---|
| 2 | 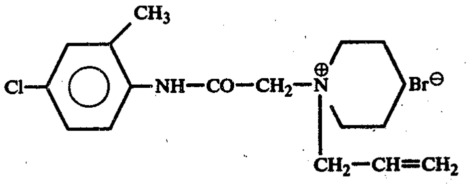 | 168-170° |
| 3 | 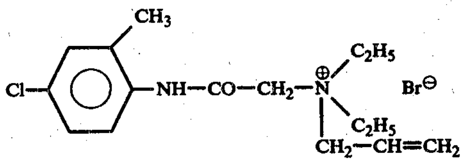 | 175-178° |
| 4 | 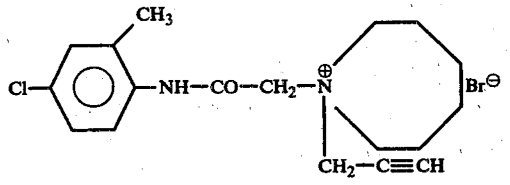 | 184-186 |

-continued
| Example | | Melting point in ° C. |
|---|---|---|
| 5 | 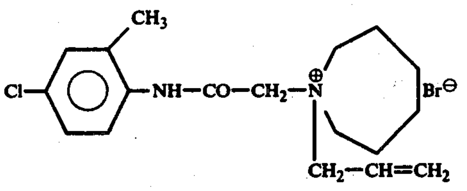 | 168–169° |
| 6 | 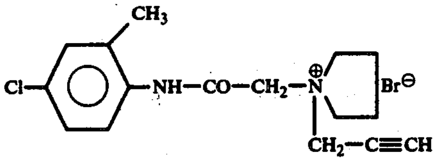 | 166–169 |
| 7 | 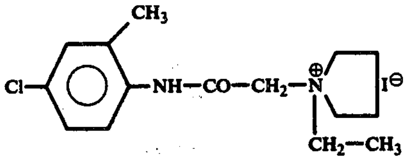 | 128–132° |
| 8 | 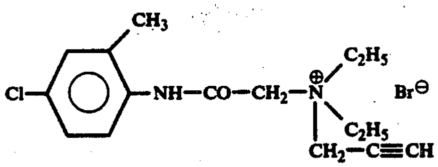 | 170–173° |
| 9 | 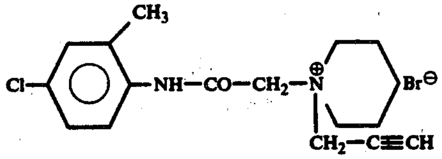 | 179–181 |
| 10 | 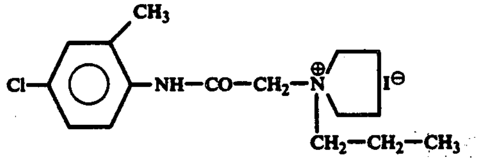 | 196–198° |
| 11 | 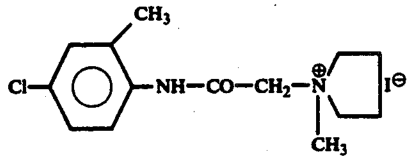 | 185–188 |
| 12 | 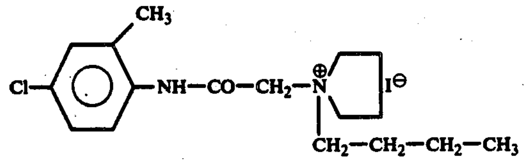 | 140–142 |
| 13 | 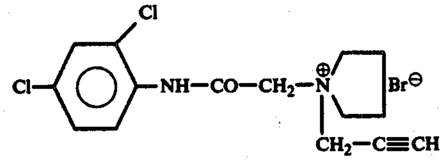 | 184–186 |
| 14 | 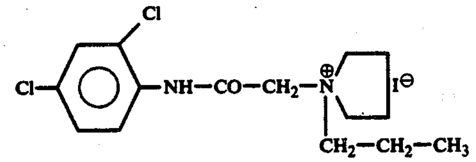 | 161–165° |

-continued
| Example | | Melting point in ° C. |
|---|---|---|
| 15 | 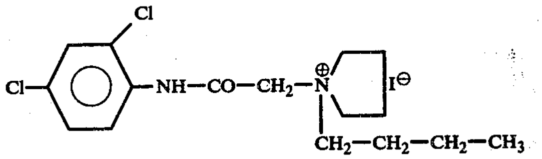 | 140–143° |
| 16 | 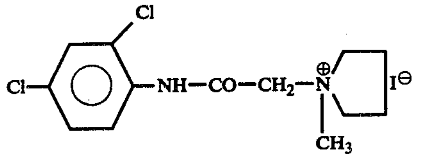 | 200–202° |
| 17 | 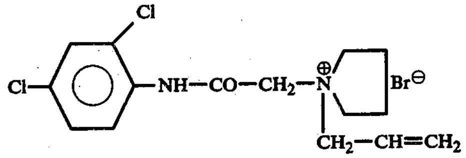 | 144–147° |
| 18 | 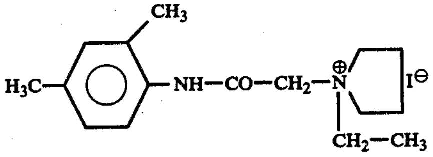 | 127–132° |
| 19 | 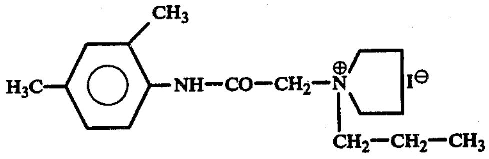 | 115–120° |
| 20 | 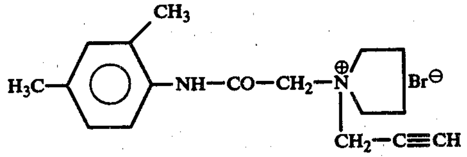 | 114–119° |
| 21 | 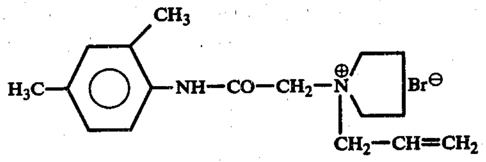 | 104–106° |
| 22 | 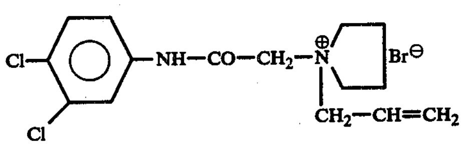 | 143–145° |
| 23 | 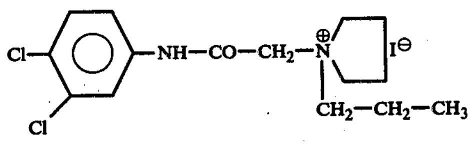 | 195–198° |
| 24 | 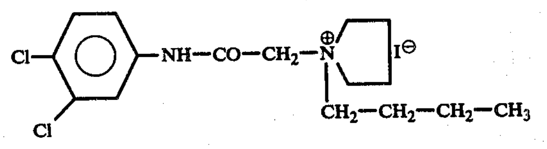 | 149–154° |
| 25 | 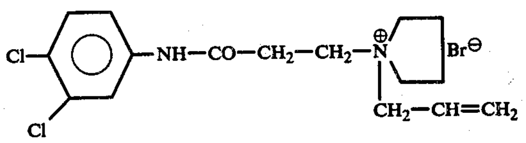 | 143–147° |

-continued
| Example | | Melting point in ° C. |
|---|---|---|
| 26 | 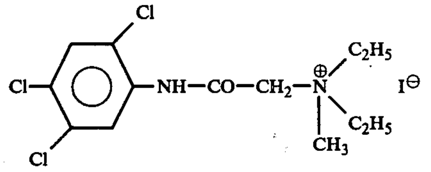 | 149-151° |
| 27 | 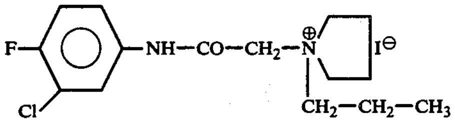 | 210-214° |
| 28 | 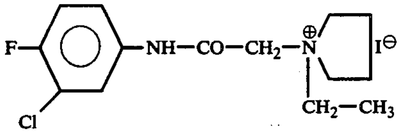 | 158-160° |
| 29 | 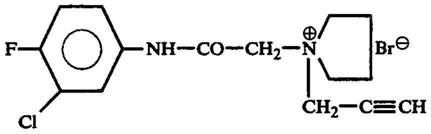 | 152-154° |
| 30 | 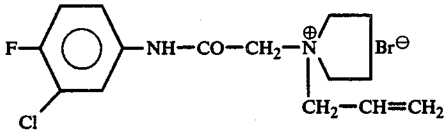 | 144-146° |
| 31 | 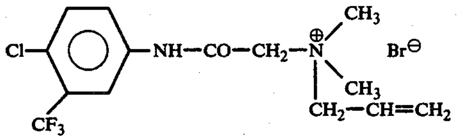 | 183-185° |
| 32 | 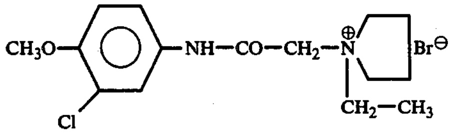 | 178-180° |
| 33 | 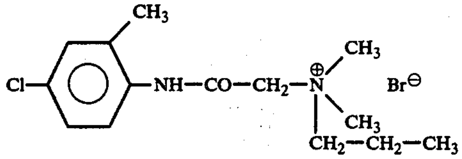 | 95-99° |
| 34 | 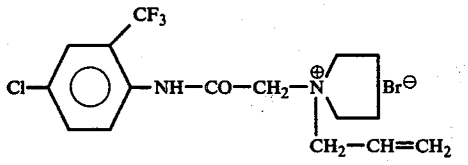 | 153-156° |
| 35 | 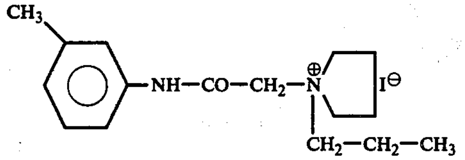 | 163-166° |
| 36 | 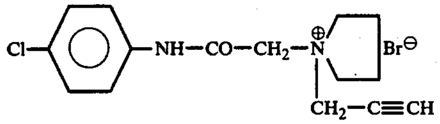 | 176-177° |

-continued
| Example | | Melting point in ° C. |
|---|---|---|
| 37 | 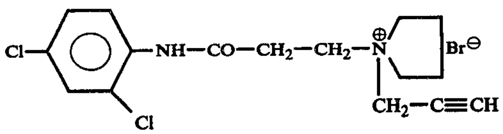 | |
| 38 | 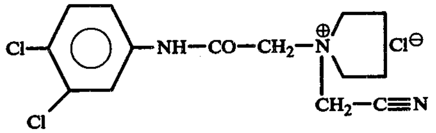 | 196–199° |
| 39 | 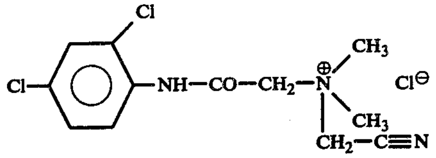 | 200–203° |
| 40 | 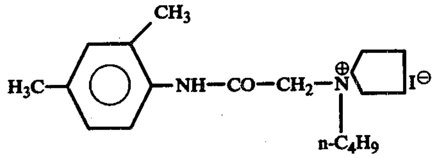 | 119–123° |
| 41 | 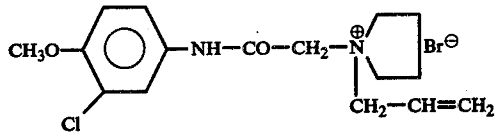 | 150–152° |
| 42 | 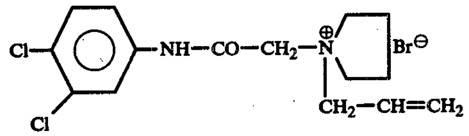 | 143–145° |
| 43 | 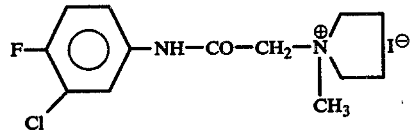 | 184–186° |
| 44 | 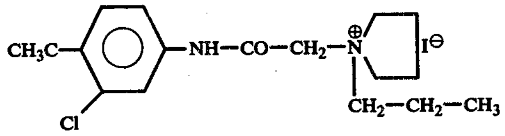 | 154–158° |
| 45 | 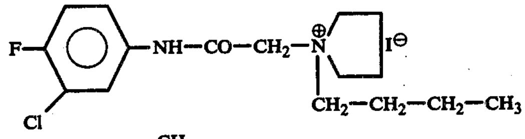 | 114–117° |
| 46 | 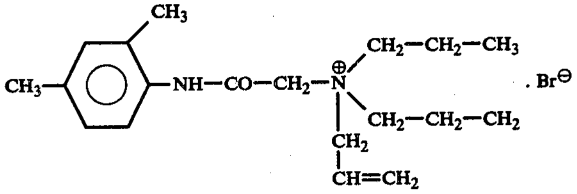 | 145°–147° |
| 47 | 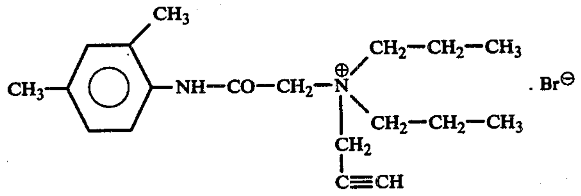 | 125°–129° |

-continued
| Example | | Melting point in ° C. |
|---|---|---|
| 48 | 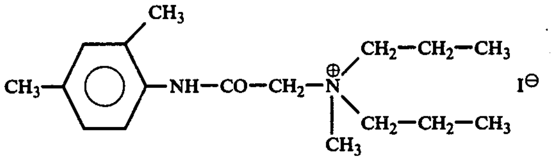 | 101°-105° |
| 49 | 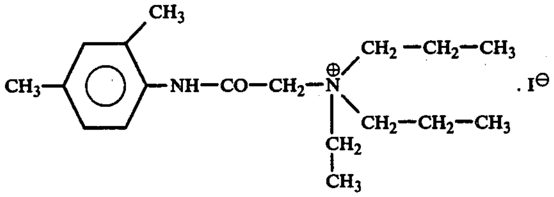 | 132°-134° |
| 50 | 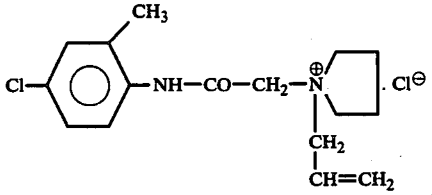 | 118°-125° |
| 51 | 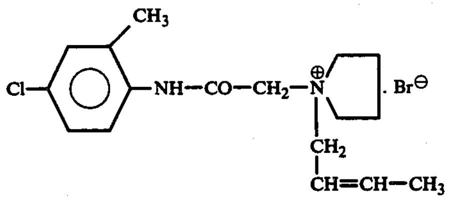 | 150°-152° |
| 52 | 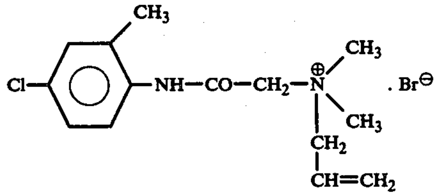 | 186°-188° |
| 53 | 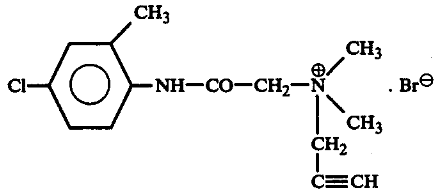 | 196°-197° |
| 54 | 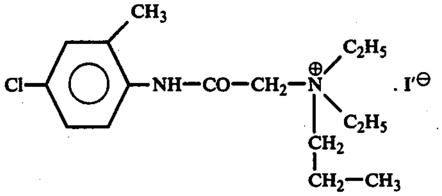 | 95°-99° |
| 55 | 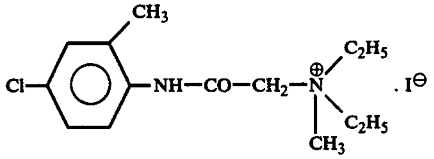 | 220°-223° |
| 56 | 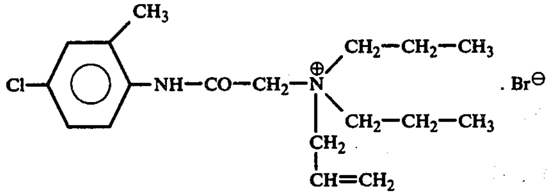 | 151°-153° |

-continued
| Example | | Melting point in ° C. |
|---|---|---|
| 57 | 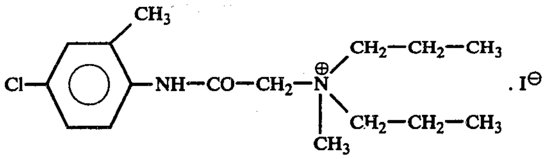 | 139°-141° |
| 58 | 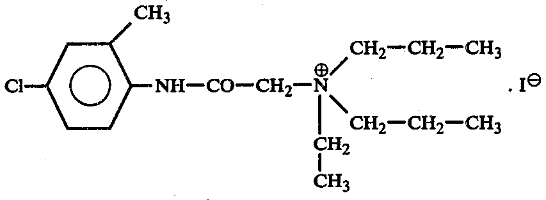 | 175°-177° |
| 59 | 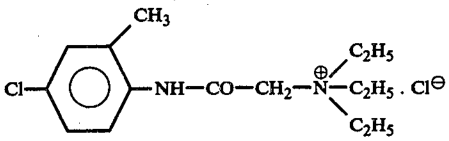 | 180°-186° C |
| 60 | 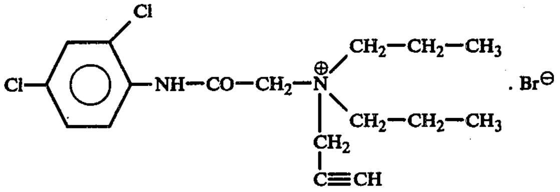 | 153°-157° C |
| 61 | 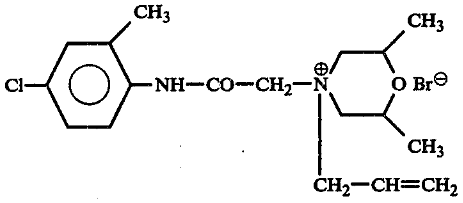 | 165-170° |
| 62 | 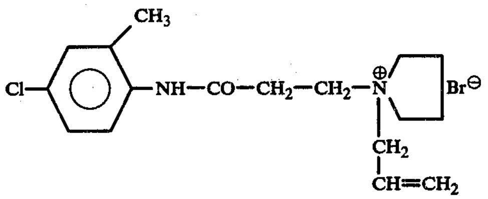 | 104-109° |
| 63 | 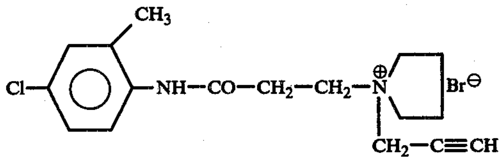 | 119-124° |
| 64 | 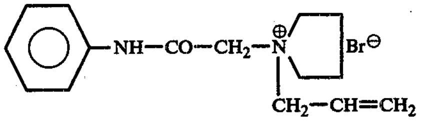 | 115-118° |
| 65 | 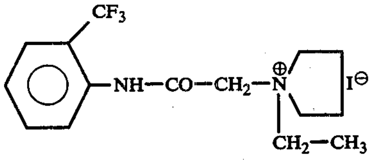 | 157-160° |
| 66 | 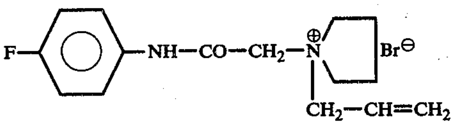 | 127-130° |

-continued
| Example | | Melting point in ° C. |
|---|---|---|
| 67 | 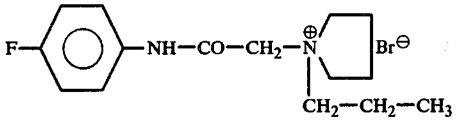 | 177-179° |
| 68 | 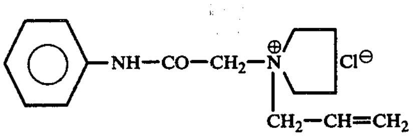 | 96-102° |
| 69 | 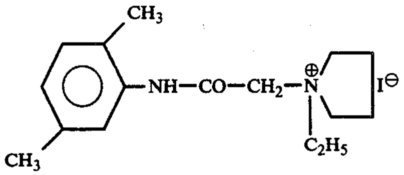 | 95-101° |
| 70 | 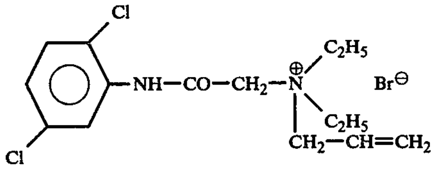 | 134-138° |
| 71 | 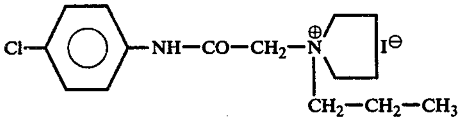 | 181-183° |
| 72 | 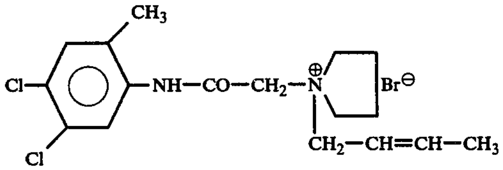 | 173-176° |
| 73 | 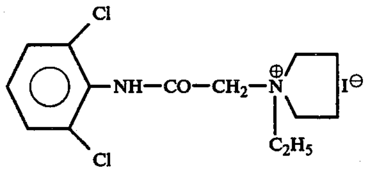 | 201-205° |
| 74 | 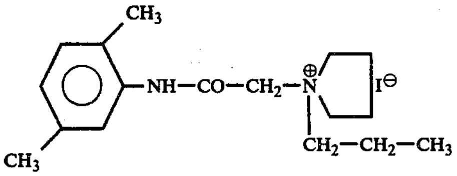 | 124-127° |
| 75 | 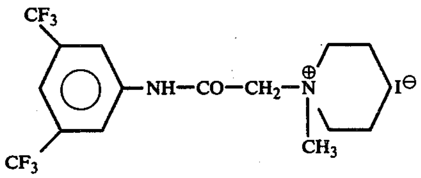 | 196-197° |
| 76 | 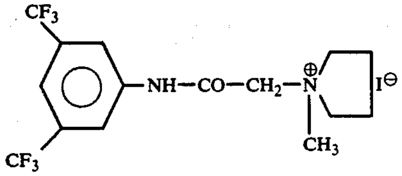 | 208-210° |

-continued
| Example | | Melting point in ° C. |
|---|---|---|
| 77 | 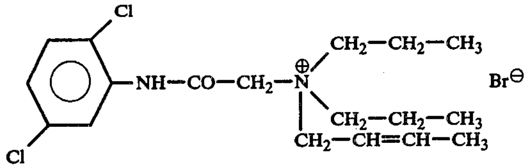 | 160–163° |
| 78 | 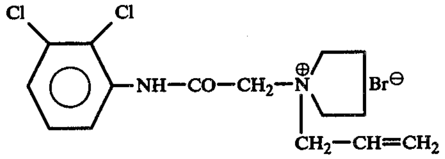 | 86–89° |
| 79 | 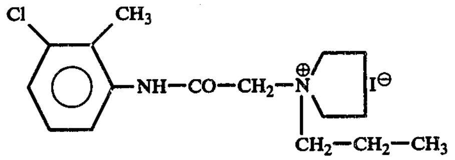 | 141–143° |
| 80 | 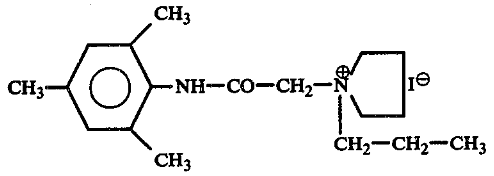 | 189–192° |
| 81 | 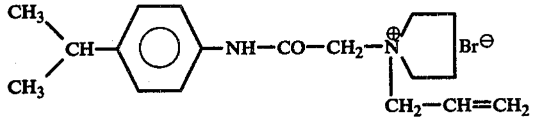 | 131–133° |
| 82 | 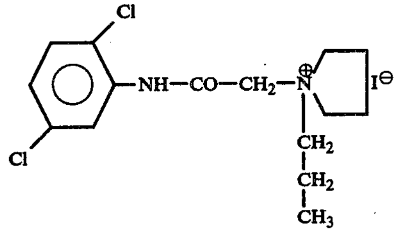 | 156–158° |
| 83 | 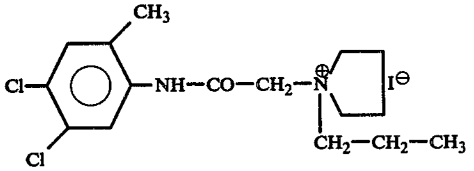 | 154–156 |
| 84 | 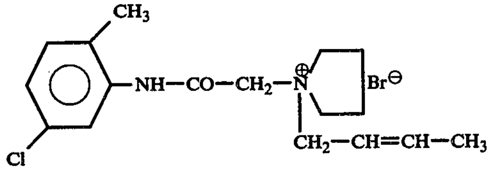 | 140–145° |
| 85 | 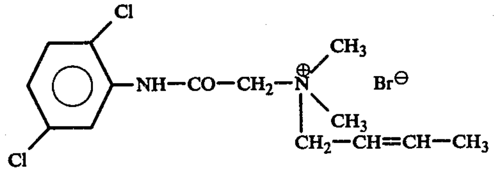 | 66–70° |
| 86 | 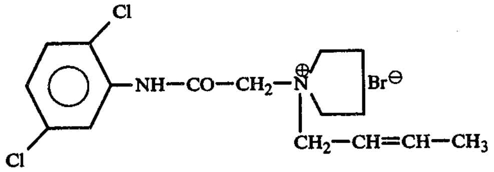 | 124–128° |

-continued
| Example | | Melting point in ° C. |
|---|---|---|
| 87 | 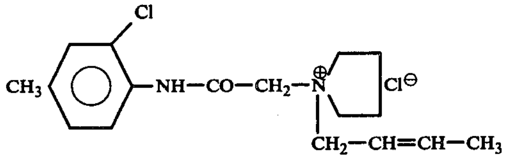 | 164–169° |
| 88 | 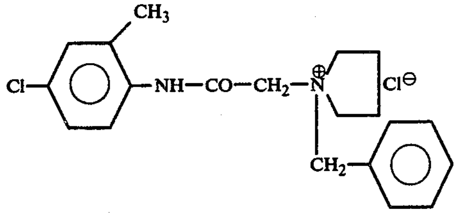 | 197–199° |
| 89 | 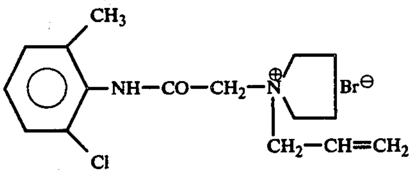 | 150–151° |
| 90 | 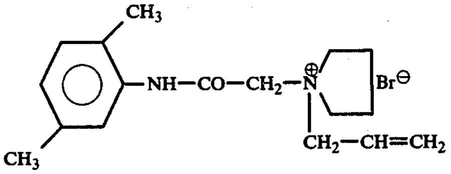 | 121–126° |
| 91 | 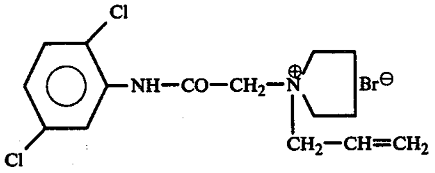 | 130–134° |
| 92 | 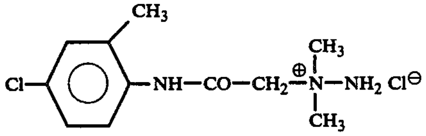 | 186–188° |
| 93 | 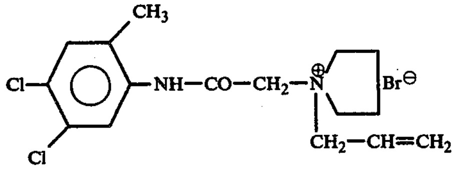 | 195–198° |
| 94 | 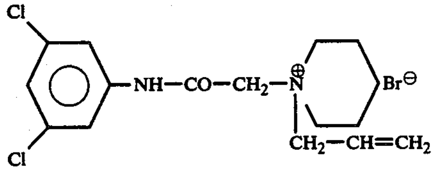 | 204–206° |
| 95 | 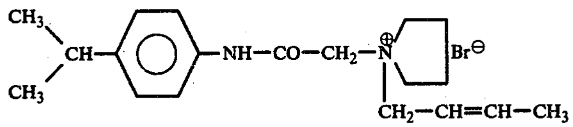 | 166–168° |
| 96 | 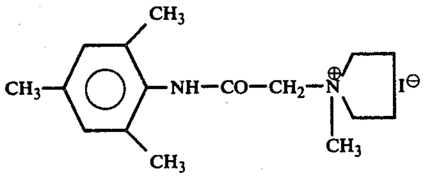 | 161–164° |

-continued
| Example | | Melting point in ° C. |
|---|---|---|
| 97 | 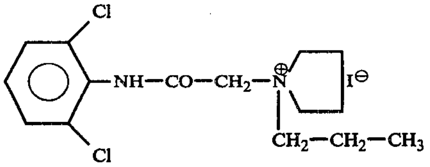 | 204–208° |
| 98 | 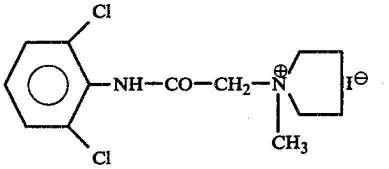 | 206–208° |
| 99 | 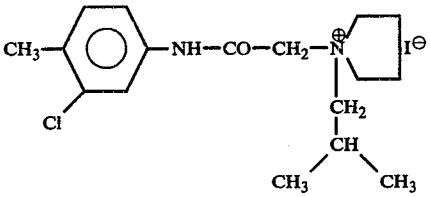 | 132–135° |
| 100 | 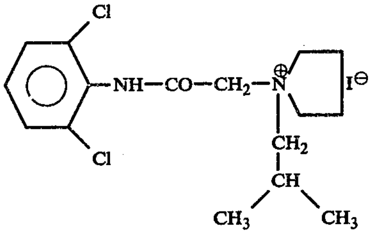 | 145–155° |
| 101 | 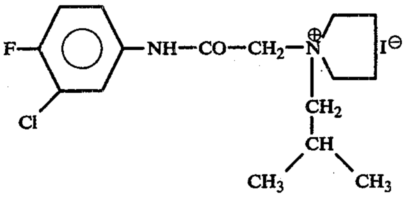 | 131–134° |
| 102 | 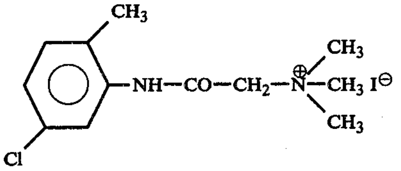 | 214–220° |
| 103 | 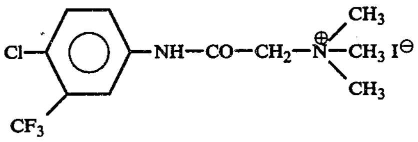 | 228–230° |
| 104 | 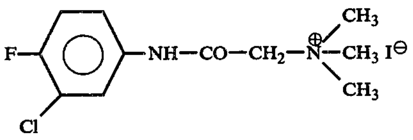 | 244–247° |
| 105 | 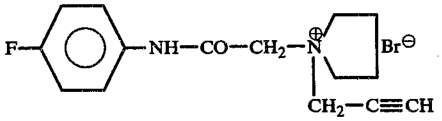 | 132–134° |
| 106 | 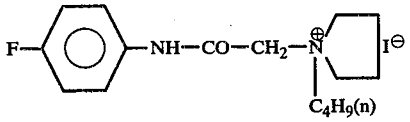 | 109–111° |

-continued
| Example | | Melting point in ° C. |
| --- | --- | --- |
| 107 | 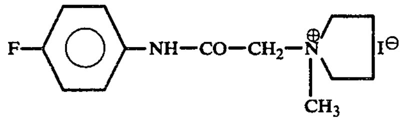 | 165-166° |
| 108 | 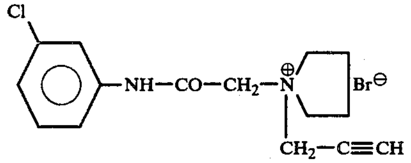 | 116-121° |
| 109 | 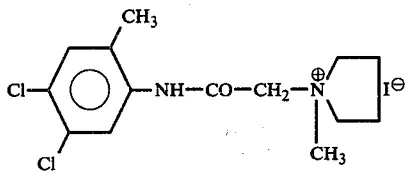 | 233-235 |
| 110 | 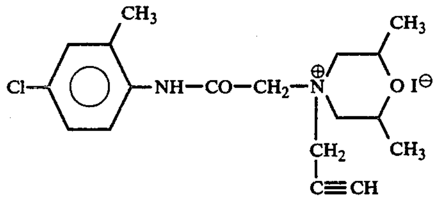 | 185-186° |
| 111 | 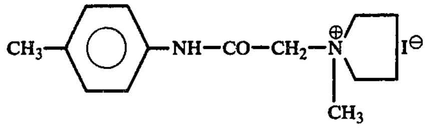 | 180-182° |
| 112 | 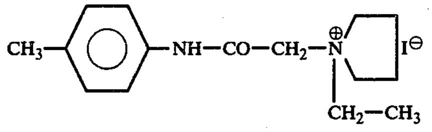 | 144-146° |
| 113 | 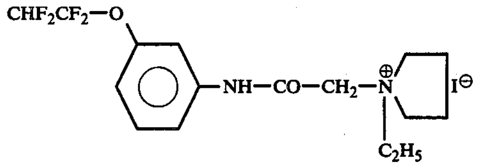 | 117-119° |
| 114 | 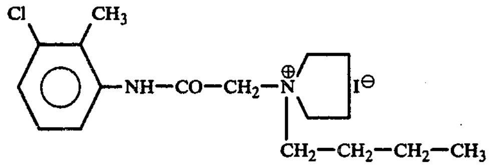 | 147-149° |
| 115 | 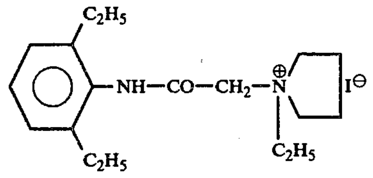 | 165-167° |
| 116 | 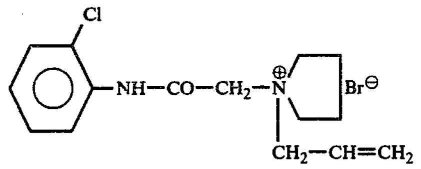 | 128-133 |

-continued
| Example | | Melting point in ° C. |
|---|---|---|
| 117 | 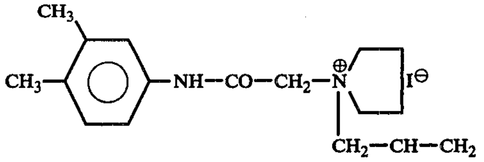 | 214–219° |
| 118 | 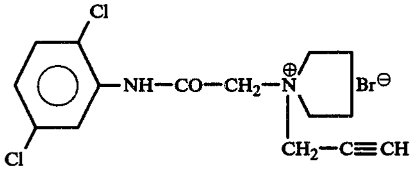 | 173–175° |
| 119 | 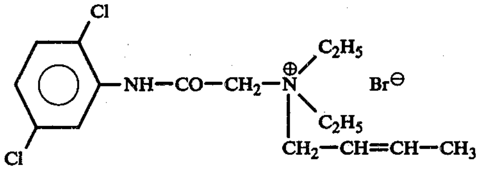 | 121–127° |
| 120 | 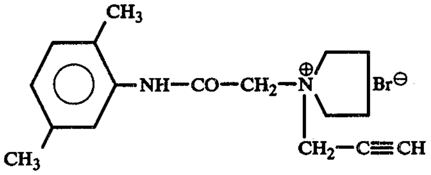 | 165–167° |
| 121 | 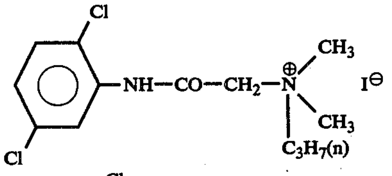 | 146–148° |
| 122 | 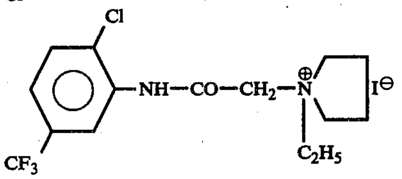 | 134–135° |
| 123 | 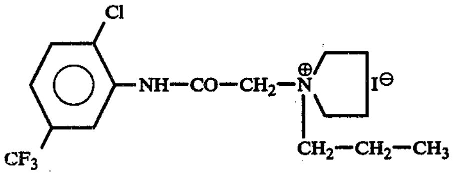 | 180–182° |
| 124 | 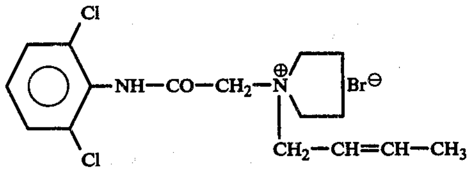 | 110–119° |
| 125 | 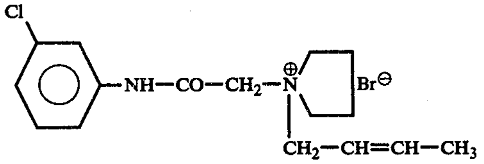 | 101–107° |
| 126 | 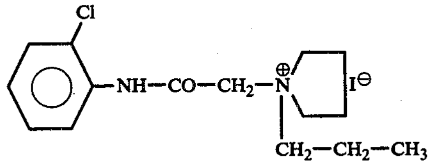 | 131–135° |

-continued
| Example | | Melting point in ° C. |
| --- | --- | --- |
| 127 | 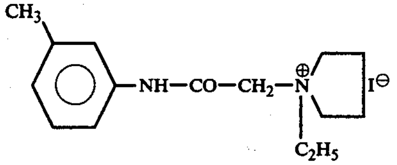 | 141-143° |
| 128 | 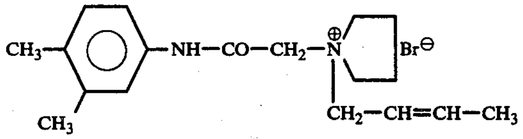 | 90-96° |
| 129 | 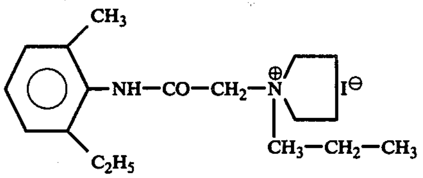 | 143-146° |
| 130 | 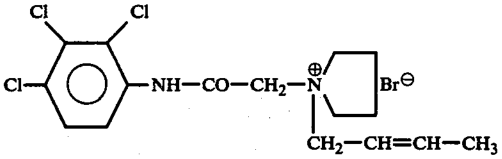 | 162-166° |
| 131 | 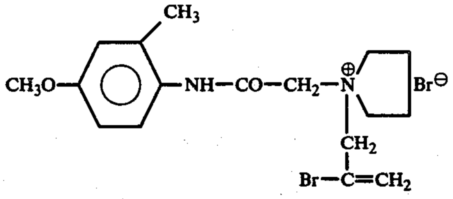 | 149-156° |
| 132 | 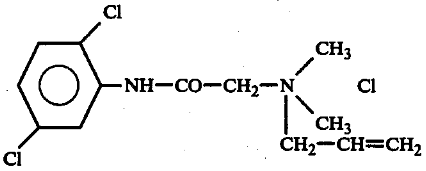 | 133-138° |
| 133 | 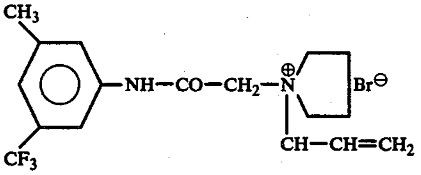 | 181° |
| 134 | 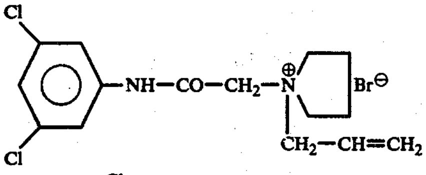 | 202-204° |
| 135 | 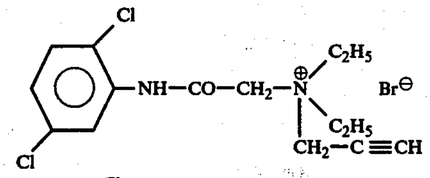 | 165-167° |
| 136 | 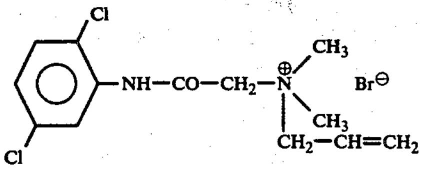 | 121-125° |

-continued
| Example | | Melting point in ° C. |
| --- | --- | --- |
| 137 | 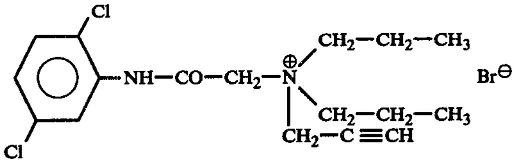 | 169–171° |
| 138 | 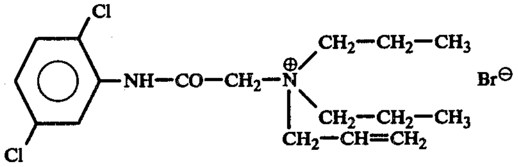 | 163–165° |
| 139 | 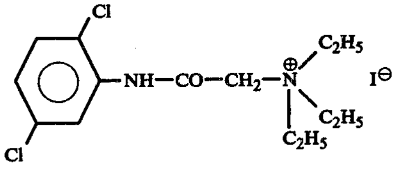 | 78–81° |
| 140 | 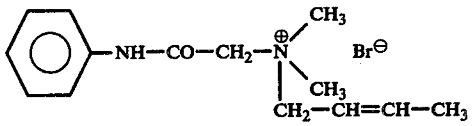 | 136–144° |
| 141 | 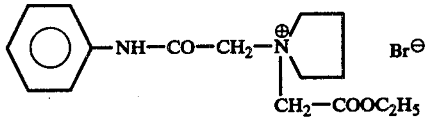 | 139–141° |
| 142 | 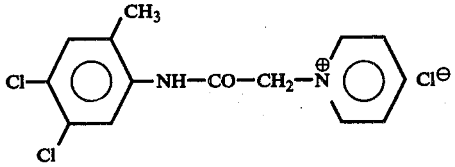 | 256–258° |
| 143 | 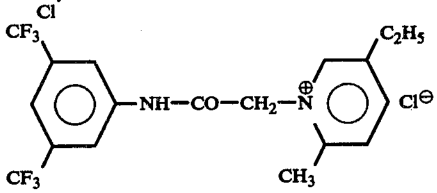 | 189–191° |
| 144 | 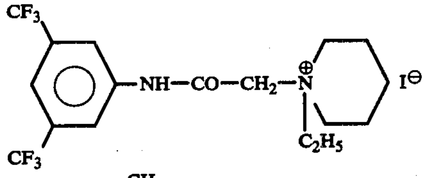 | 183–185° |
| 145 | 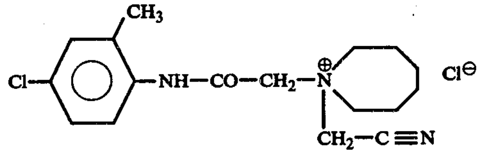 | 210–212° |
| 146 | 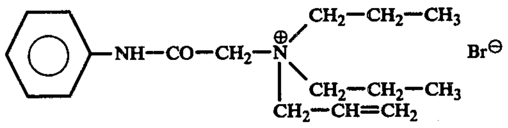 | 145–148° |
| 147 | 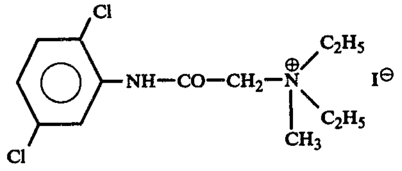 | 138–141° |

-continued
| Example | | Melting point in ° C. |
|---|---|---|
| 148 | 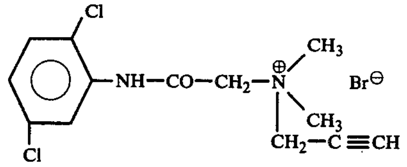 | 142–146° |
| 149 | 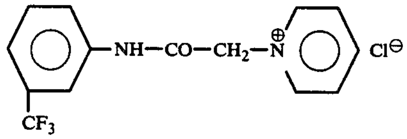 | 212–215° |
| 150 | 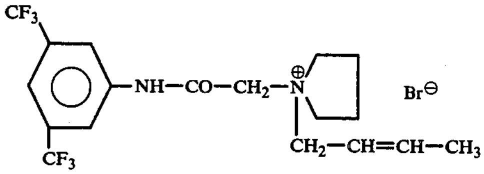 | 166–168° |
| 151 | 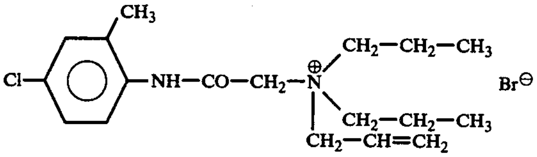 | 151–153° |
| 152 | 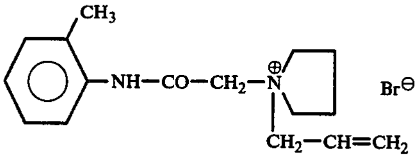 | 129–133° |
| 153 | 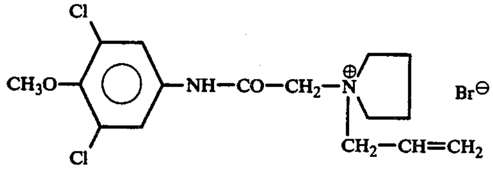 | 191–194° |
| .54 | 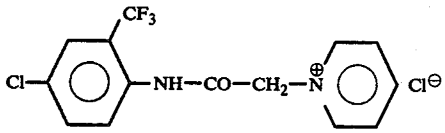 | 220–223° |
| 55 | 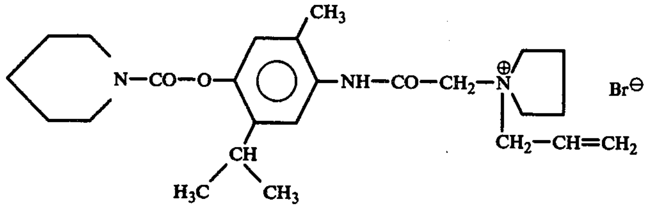 | |
| 56 | 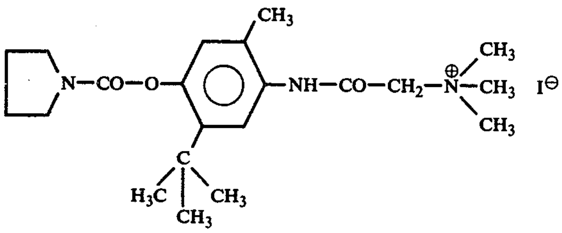 | |

-continued
| Example | | Melting point in ° C. |
|---|---|---|
| 157 | 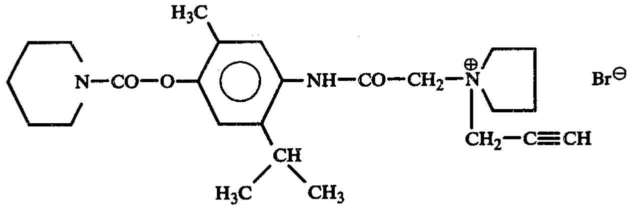 | |
| 158 | 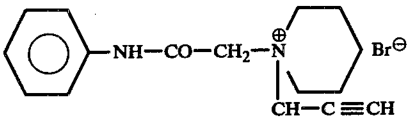 | |
| 159 | 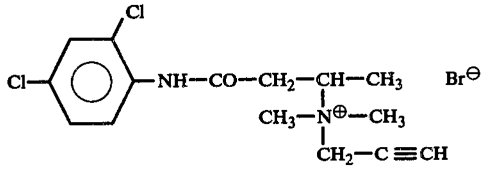 | |
| 160 | 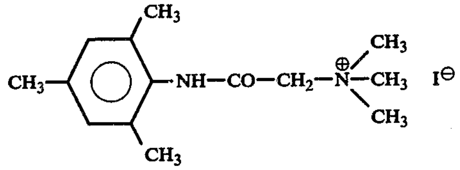 | |
| 161 | 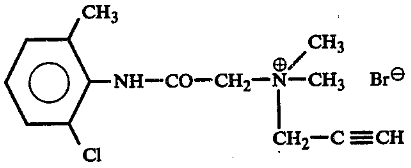 | |
| 162 | 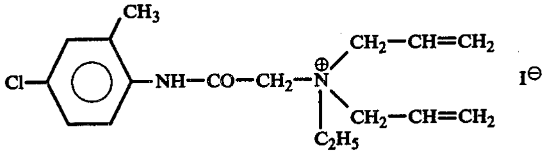 | |
| 163 | 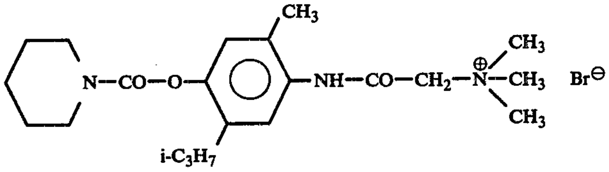 | |
| 164 | 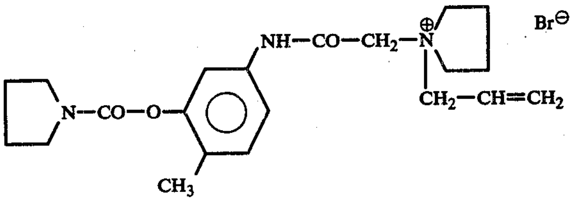 | |
| 165 | 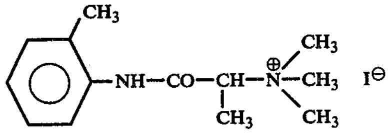 | |
| 166 | 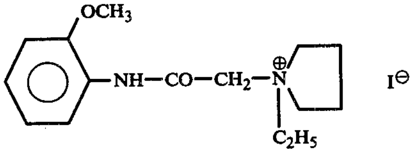 | |

-continued
| Example | | Melting point in ° C. |
|---|---|---|
| 167 | 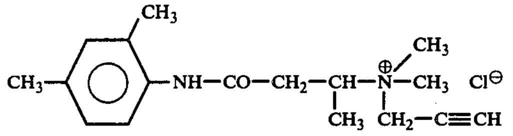 | |
| 168 | 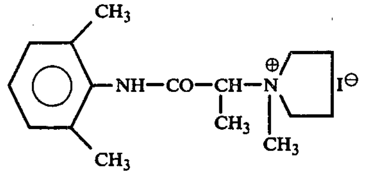 | |
| 169 | 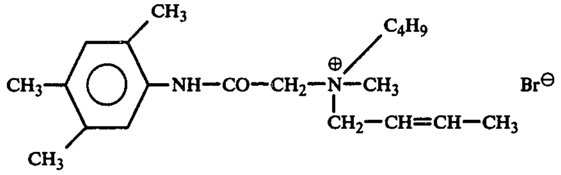 | |
| 170 | 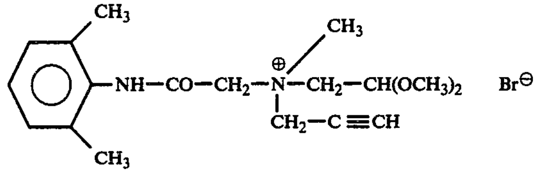 | |
| 171 | 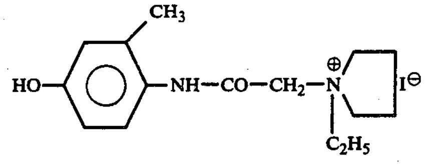 | |
| 172 | 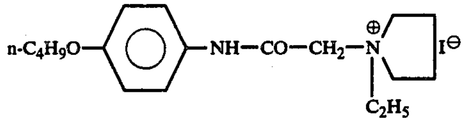 | |
| 173 | 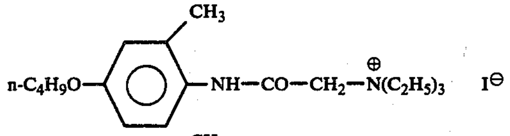 | |
| 174 | 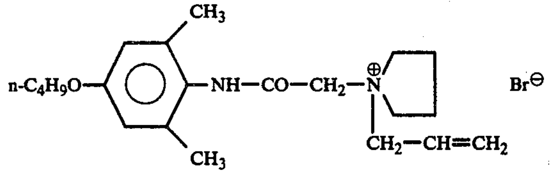 | |
| 175 | 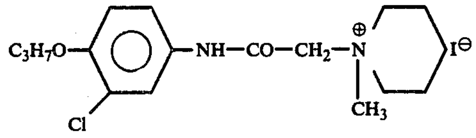 | |
| 176 | 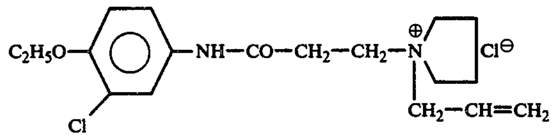 | |
| 177 | 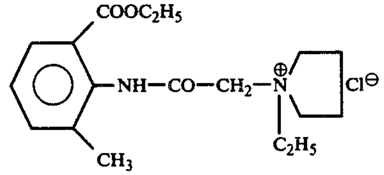 | |

-continued
| Example | | Melting point in ° C. |
|---|---|---|
| 178 | 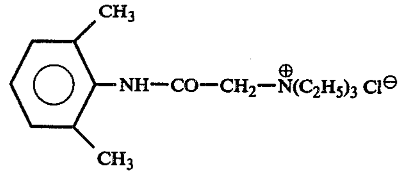 | |
| 179 | 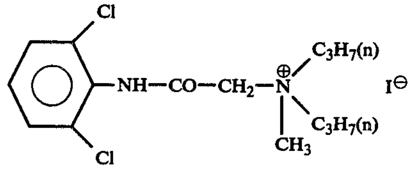 | |
| 180 | 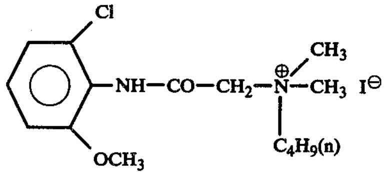 | |
| 181 | 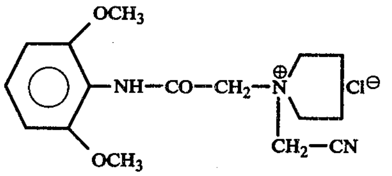 | |
| 182 | 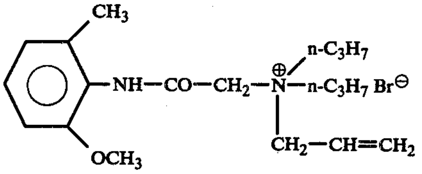 | |
| 183 | 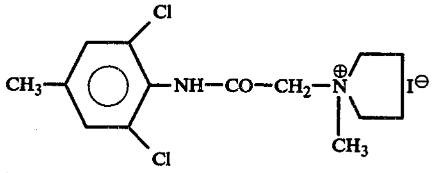 | |
| 184 | 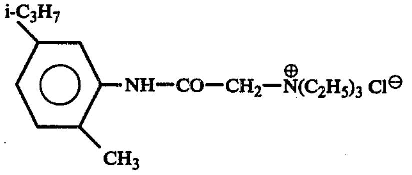 | |
| 185 | 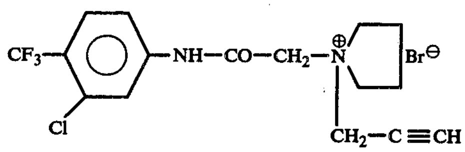 | |
| 186 | 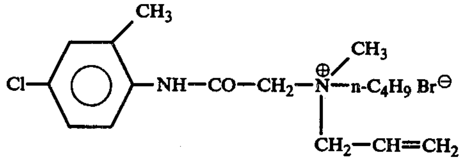 | |
| 187 | 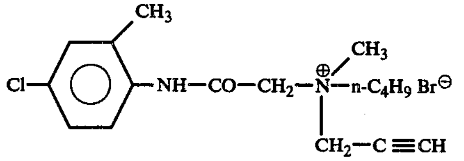 | |

-continued
| Example | | Melting point in ° C. |
|---|---|---|
| 188 | 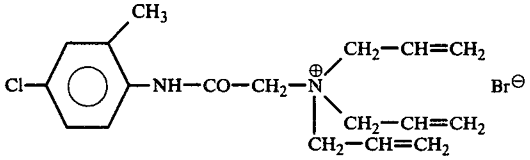 | |
| 189 | 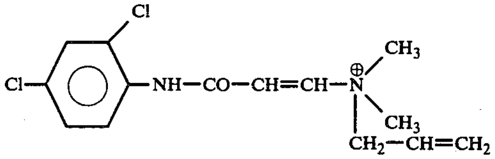 | |
| 190 | 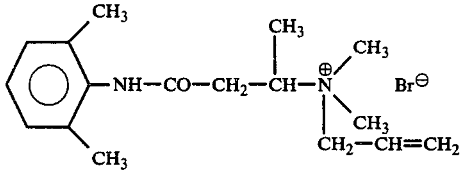 | |
| 191 | 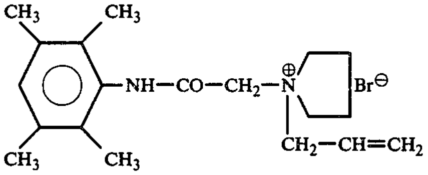 | |
| 192 | 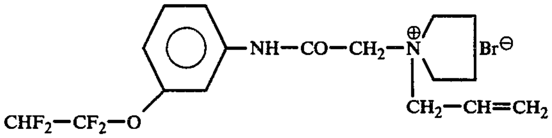 | |
| 193 | 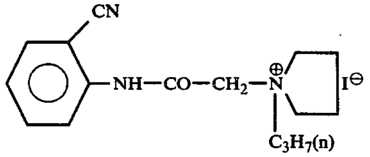 | |
| 194 | 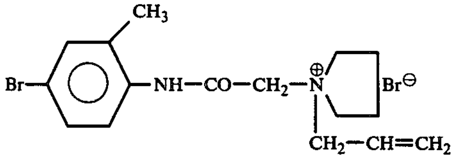 | |
| 195 | 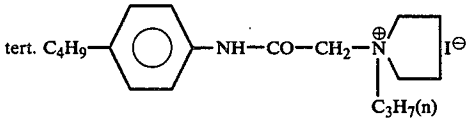 | |
| 196 | 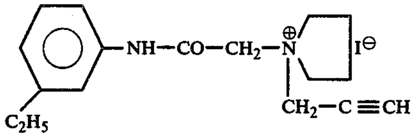 | |
| 197 | 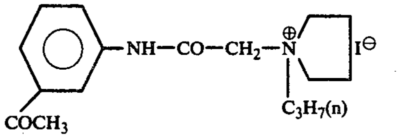 | |
| 198 | 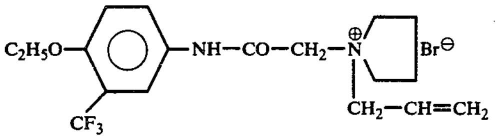 | |

-continued
| Example | | Melting point in ° C. |
| --- | --- | --- |
| 199 | 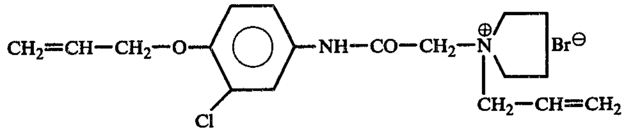 | |
| 200 | 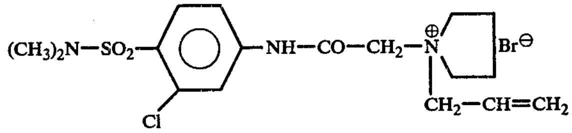 | |
| 201 | 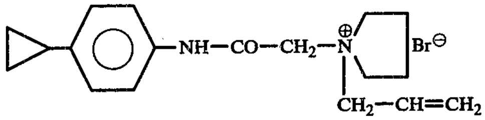 | |
| 202 | 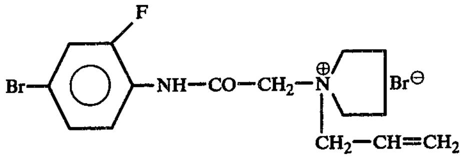 | |
| 203 | 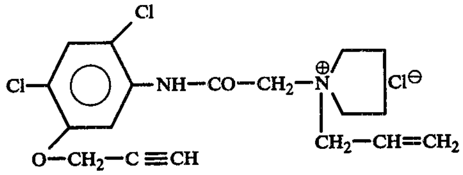 | |
| 204 | 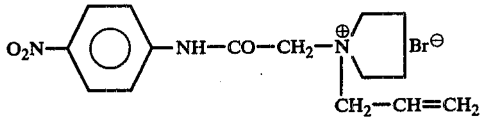 | |
| 205 | 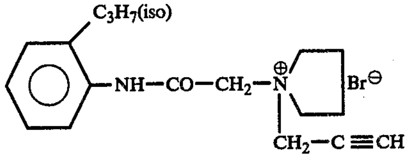 | |
| 206 | 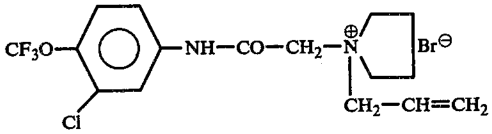 | |
| 207 | 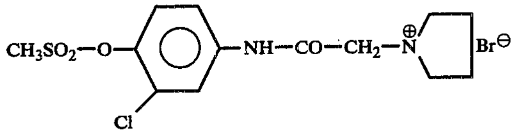 | |
| 208 | 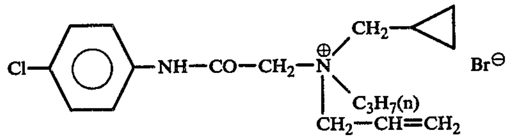 | |
| 209 | 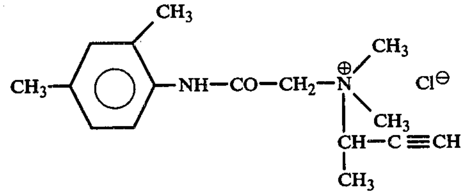 | |

-continued
| Example | | Melting point in ° C. |
| --- | --- | --- |
| 210 | 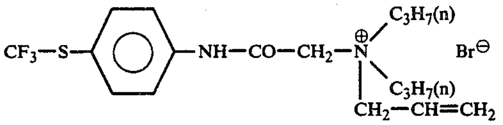 | |
| 211 | 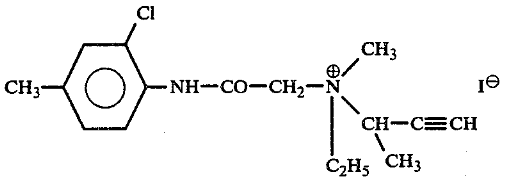 | |
| 212 | 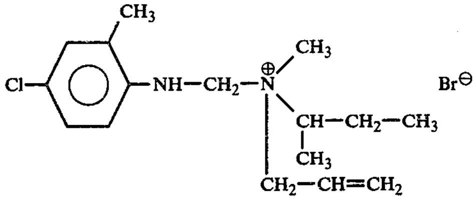 | |
| 213 | 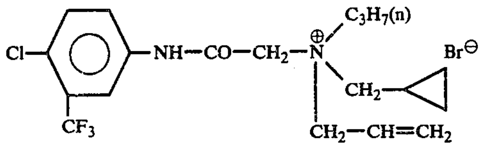 | |
| 214 | 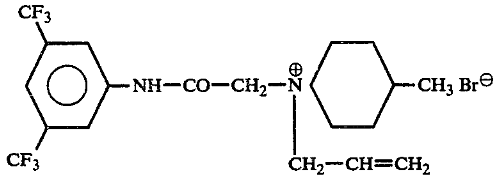 | |
| 215 | 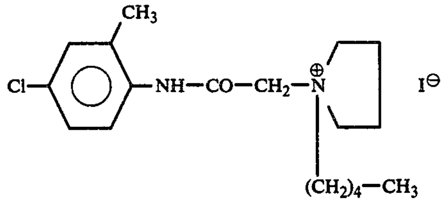 | 116–120° |
| 216 | 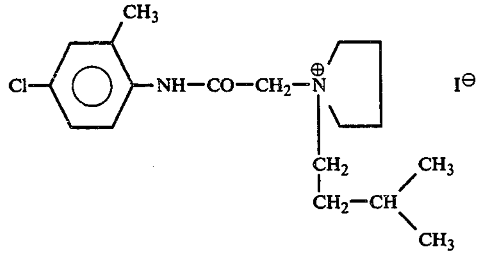 | 155–159° |
| 217 | 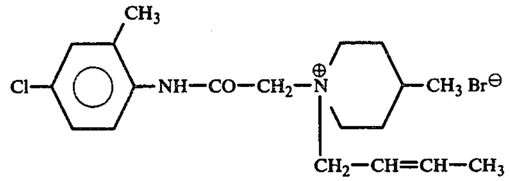 | 187–190° |
| 218 | 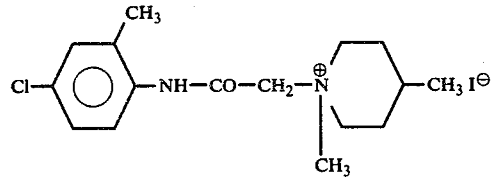 | 186–189° |

-continued
| Example | | Melting point in ° C. |
|---|---|---|
| 219 | 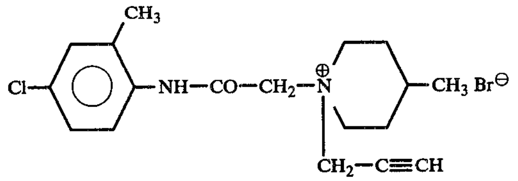 | 170–173 |
| 220 | 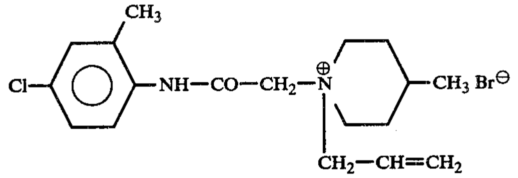 | 174–178° |
| 221 | 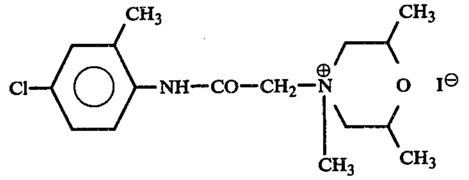 | 169–170° |
| 222 | 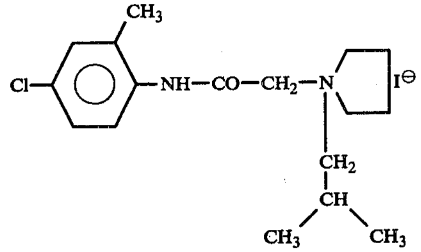 | 168–172° |
| 223 | 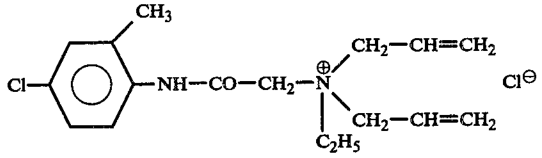 | 147–150 |
| 224 | 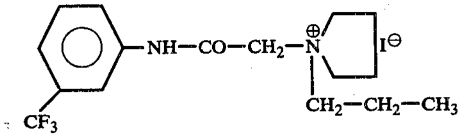 | 116–118° |
| 225 | 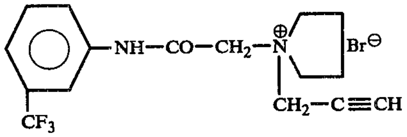 | 186–188° |
| 226 | 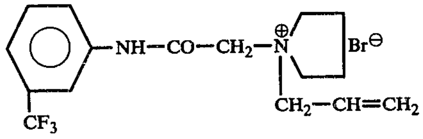 | 112–113° |
| 227 | 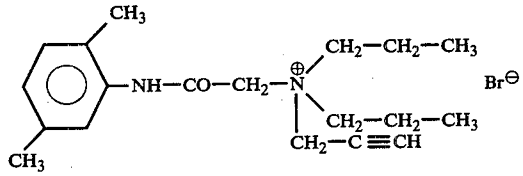 | 166–168° |

-continued

| Example | | Melting point in ° C. |
|---|---|---|
| 228 | 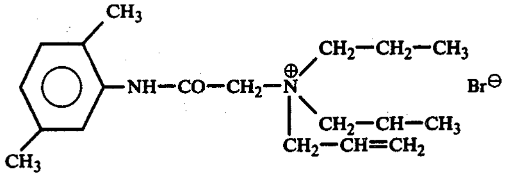 | 169-170° |
| 229 | 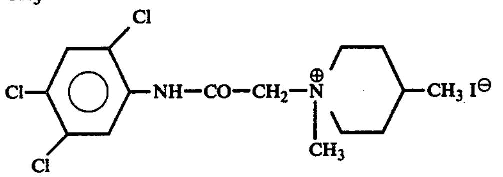 | 207-210° |
| 230 | 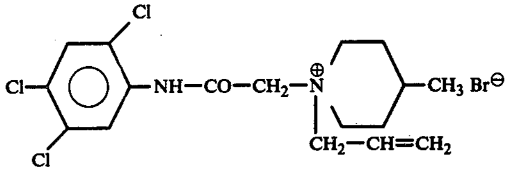 | 176-178° |
| 231 | 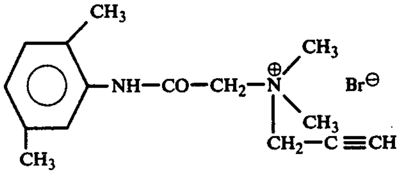 | 136-140° |
| 232 | 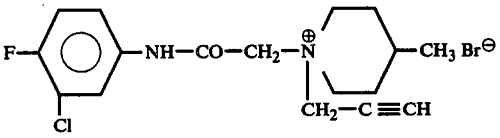 | 140-145° |
| 233 | 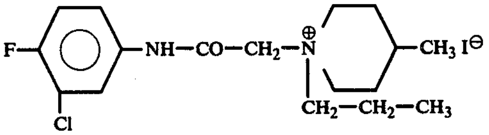 | 164-168° |
| 234 | 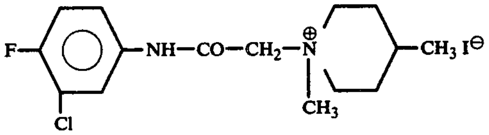 | 200 -204° |
| 235 | 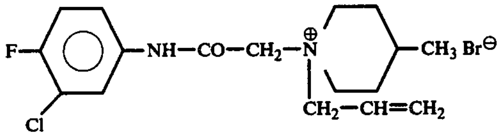 | 179-182° |
| 236 | 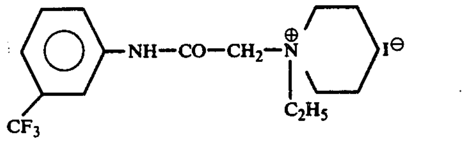 | 160-162° |
| 237 | 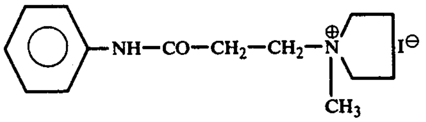 | 178-180° |

The compositions according to the invention are obtained in known manner by intimately mixing and/or grinding active substances of the formula I with suitable carriers, with or without the addition of dispersants or solvents which are inert towards the active substances.

The active substances may take and be used in the following application forms:

Solid forms: dusts, tracking agents, granules, coated granules, impregnated granules and homogeneous granules; active substance concentrates which are dispersible in water: wettable powders, pastes, emulsions; emulsion concentrates.

Liquid forms: solutions.

Solid forms (dusts, tracking agents, granules) are obtained by mixing the active substances with solid carriers. Suitable carriers are, for example: kaolin, talc, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulphates, magnesium oxide, ground synthetic materials, fertilisers. for example ammonium sulphate, ammonium phosphate, ammonium nitrate, urea, ground vegetable products, such as corn meal, bark dust, sawdust, nutshell meal, cellulose powder residues of plant extractions, activated charcoal etc. These substances can either be used singly or in admixture with one another.

The granular size of the carriers for dusts is advantageously up to approx. 0.1 mm, for tracking agents approx. 0.075 to 0.2 mm, and for granules 0.2 mm or greater.

The concentration of active substance in the solid forms are 0.5 to 80%.

To these mixtures can also be added additives which stabilize the active substance and/or nonionics, anionics and cationics, which, for example, improve the adhesion of the active ingredients on plants or parts of plants (tackifiers and agglutinants) and/or ensure a better wettability (wetting agents) and dispersibility (dispersing agents). Examples of suitable aggentinents are: olein/-chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl moiety, lignin sulphonic acids, the alkali metal and alkaline earth metal salts thereof, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of urea and formaldehyde, and also latex products.

Water-dispersible concentrates, i.e. wettable powders, pastes and emulsifiable concentrates, are compositions which can be diluted with water to the desired concentration. They consist of active substance, carrier, optionally additives which stabilize the active substance, surface-active substances and anti-foam agents and, if appropriate, solvents. The concentrations of active substance in these compositions is 5 to 80%.

Wettable powders and pastes are obtained by mixing and grinding the active substances with dispersing agents and pulverulent carriers in suitable devices until homogeneity is attained. Suitable carriers are, for example, those already mentioned for the solid forms of application. In some cases it is advantageous to use mixtures of different carriers. As dispersing agents there can be used, for example, condensation products of sulphonated naphthalene and sulphonated naphthalene derivatives with formaldehyde, condensation products of naphthalene or naphthalene sulphonic acids with phenol and formaldehyde, as well as alkali metal, ammonium and alkaline earth metal salts of lignin sulphonic acid, in addition, alkylaryl sulphonates, alkali metal and alkaline earth metal salts of dibutyl naphthalene sulphonic acid, fatty alcohol sulphates such as salts of sulphated hexadecanols, heptadecanols, octadecanols, and salts of sulphated fatty alcohol glycol ethers, the sodium salt of oleyl methyl tauride, ditertiary acetalene glycols, dialkyl dilauryl ammonium chloride and fatty acid alkali metal and alkaline earth metal salts.

Suitable anti-foam agents are for example silicones.

The active substance is so mixed, ground sieved and strained with the additives mentioned above that, in wettable powders, the solid particle size of 0.02 to 0.04 mm and in pastes, of 0.02 mm, is not exceeded. Emulsion concentrates and pastes are manufactured by using dispersing agents, such as those cited previously above, organic solvents, and water. Examples of suitable solvents are: alcohols, benzene, xylenes, toluene, dimethyl sulphoxide, and mineral oil fractions which boil between 120° and 350° C. The solvents must be practically odourless, not phytotoxic, inert to the active substances and not readily inflammable.

Furthermore, the agents according to the invention can be applied in the form of solutions. For this purpose the active substances or several active substances of the general formula I are dissolved in suitable organic solvents, mixtures of solvents, or in water. Aliphatic and aromatic hydrocarbons, chlorinated derivatives thereof, alkylnaphthalenes and mineral oils, by themselves or in admixture, can be used as organic solvents. The solutions will contain the active substances in a concentration from 1 to 20%.

These solutions can be applied either by means of a propellant gas (as spray) or with special sprays (as aerosol).

The compositions of this invention can be mixed with other biocidally active substances of agents. Thus in order to broaden the activity spectrum the compositions may contain, for example, insecticides, fungicides, bactericides, fungistats, bacteriostats or nematocides, in addition to the cited compounds of the formula I. The compositions of the invention may also contain plant fertilisers, trace elements etc.

Formulations of the novel active compounds of the formula I are described hereinafter. The parts denote parts by weight.

Granules

The following substances are used to produce 5% granules:

5 parts of active substance,
0.25 parts of epichlorohydrin,
0.25 parts of cetyl polyglycol ether,
3.50 parts of polyethylene glycol ("Carbowax"),
91 parts of kaolin (particle size 0.2–0.8 mm).

The active substance is mixed with epichlorohydrin and dissolved with 6 parts of acetone; the polyethylene glycol and cetyl polyglycol ether are then added. The resultant solution is sprayed on kaolin, and the acetone is subsequently evaporated in vacuo.

The resultant granules are particularly suitable for incorporation into the soil which is intended for rearing ornamental plant cuttings whose growth is to be inhibited.

Wettable powder

The following constituents are used for the preparation of (a) a 40%, (b) a 50%, (c) a 25%, and (d) a 10% wettable powder:

(a)

40 parts of active substance (28), 5 parts of sodium lignin sulphonate,
1 part of sodium dibutyl-naphthalene sulphonate,
54 parts of silicic acid.

(b)

50 parts of active substance (3),
5 parts of alkylarylsulphonate ("Tinovetin B"),
10 parts of calcium ligninsulphonate,
1 part of a mixture of Champagne chalk/hydroxyethyl cellulose mixture (1:1),
20 parts of silicic acid,
14 parts of kaolin.

(c)

25 parts of active substance (1),
5 parts of the sodium salt of oleylmethyltauride,
2.5 parts of naphthalenesulphonic acid/formaldehyde condensate,
0.5 part of carboxymethyl cellulose,
5 parts of neutral potassium aluminium silicate,
62 parts of kaolin.

(d)

10 parts of active substance (14),
3 parts of a mixture of the sodium salts of saturated fatty alcohol sulphates,
5 parts of naphthalenesulphonic acid/formaldehyde condensate,
82 parts of kaolin.

The active substances are homogeneously mixed in suitable mixers with the additives and the mixture is then ground in appropriate mills and rollers. Wettable powders are obtained which can be diluted with water to give suspensions of the desired concentration. Such suspensions can be used for example for removing undesired suckers, for tillering grass plots, for inhibiting the growth of soya, cuttings, etc.

Emulsion Concentrate

The following ingredients are mixed to prepare 25% emulsion concentrates:

(a)

25 parts of active substance (1),
5 parts of a mixture of nonylphenolpolyoxyethylylene and calcium dodecylbenzenesulphonate,
70 parts of xylene.

(b)

25 parts of active substance (31),
10 parts of a mixture of nonylphenolpolyoxyethylene and calcium dodecylbenzenesulphonate,
65 parts of cyclohexanone.

This concentrate can be diluted with water to give suitable concentrations. Such emulsions are suitable for inhibiting the growth of grasses, cereals, soya, ornamentals, the second being also especially suitable for promoting the abscission of fruit and leaves.

As has already been mentioned, the compositions of the present invention are suitable for inhibiting the vegetative growth of mono- and dicotyledonous plants by imparting a more compact form to these plants. The active compounds of the compositions have only a low toxicity to warm-blooded animals and, when used in reasonable amounts, cause no damage to the plants. The novel compositions and the active compounds contained therein retard the vegetative growth, promote blossoming, the ripening of fruit and the formation of separation tissue.

The principal field of use of these compositions of the present invention is the inhibition of growth in cultures of soya and other leguminosae, in tobacco plants, cereals, and also in ornamentals, bushes (hedgerows) and trees, and also the inhibition of the growth of vegetation along road shoulders, canal embankments, in airports, turf for sporting activities, and in ornamental grass plots and fruit plantations.

By inhbiting growth it is possible, for example, to sow the plants in soya cultures in more narrowly spaced rows, which in turn makes a greater yield possible per unit of area. The plants are of smaller growth, develop strong green leaves and, in proportion to the leaves, a greater blossoming and set of fruit. The tighter spacing of the plants affords better protection against their being beaten to the ground by rain and wind.

In tobacco plants, the growth inhibition prevents chiefly the formation of side-shoots or suckers, a factor which aids the development of large strong leaves.

The application of the compositions of the invention effects in grass a slower growth, whereby for example areas of grass need be cut less often. Shorter, strong stalks are formed in cereals, which are thereby made more stable.

The growth inhibition of ornamental plants and shrubs results in smaller plants of regular proportions with shorter stalks. Ornamental shrubs require less frequent cutting.

The extent and nature of the action depend on a wide variety of factors according to the species of the plant, in particular on the application concentration, and the time of application with regard to the development stage of the plant. The active substances are applied preferably in the form of liquid compositions both to the parts of plants above the soil and to those on or in the soil. The application to the parts of plants above the soil is preferred, for which purpose solutions or aqueous dispersons are most suitable.

The rates of applications must be adapted to the cultivated plant, the time of application and are advantageously between 0.01 and 2 kg per hectare.

A number of the active substances of the formula Ia listed in the above examples are preferred for specific fields of use.

Active substances 25, 26 and 28, and also 1, 15, 21 and 30 are particularly suitable for inhibiting the growth of grasses.

Active substances 1 to 7, 13, 14 and 18 are preferred growth inhibitors in soya.

Active substances 1, 6, 7, 10 to 16, 18 to 24, 26, 27, 30 and 40 have proved particularly useful as growth inhibitors in ornamentals.

Active substances 1, 2, 4 and 21 are particularly useful for inhibiting growth in cereals, whilst active substances 17, 28 and 31 also have a good fruit abscission action.

Growth inhibition in grasses (post-emergence method)

Seeds of the grasses *Lolium perenne, Poa pratensis, Festuca ovina,* and *Dactylis glomerata* were sown in plastic dishes filled with an earth/turf/sand mixture. After 3 weeks the emergent grasses were cut back to a height of 4 cm above the soil and 2 days later sprayed with aqueous spray broths of active substances 26 and 28. The amount of active substance corresponded to a rate of application of 5 kg of active substance per hectare. Fourteen days after application the growth of the grasses was evaluated according to the following linear rating:

1 = strong inhibition (no growth from the time of application)

9 = no inhibition (growth as untreated control)

The following results were obtained:

| Compound | Inhibition rating *Lolium perenne* | *Poa pratensis* | *Festuca ovina* | *Dactylis glomerata* |
|---|---|---|---|---|
| Control | 9 | 9 | 9 | 9 |
| 28 | 6 | 4 | 4 | 4 |
| 26 | 6 | 2 | 3 | 4 |

Inhibition of the growth of meadow grass and plants

At the start of the growth of vegetation in the spring, 10 $m^2$ parcels of a meadow with thick growth were sprayed with aqueous preparations of active substance 1. The growth in height of the individual plant species was determined 4 weeks later and compared with the growth in height at the time of application.

The following results were obtained:

| Species of plant | % age inhibition of growth compared with the control: 5 kg of active substance/hectare | 2.5 kg of active substance/hectare |
|---|---|---|
| *Holcus lanatus* | 90% | 20% |
| *Poa pratensis* | 80% | 40% |
| *Plantago lanceolata* | 80% | 10% |
| *Trifolium pratense* | 80% | 30% |
| *Vicia hirsuta* | 100% | 30% |
| *Taraxacum officinale* | 80% | 70% |
| *Rumex obtusifolius* | 80% | 60% |

Inhibition of growth in cereals (post-emergence application, increase in stability)

Seeds of wheat and rye were sown in earthenware pots. One week after emergence, the plants were sprayed with an aqueous preparation of active substance 2. The amount of active substance was equivalent to 6 and 2 kg/ha respectively.

The test was evaluated 3 weeks later by determining the growth in height of the treated and untreated plants. The following results were obtained:

| Treatment | Growth in height: wheat | rye |
|---|---|---|
| Control (untreated) | 40 cm | 38 cm |
| 6 kg AS/ha | 21 cm | 20 cm |
| 2 kg AS/ha | 23 cm | 32 cm |

Inhibition of the vegetative growth of soya plants

Soya plants of the variety "Hark" were reared in earthenware pots and sprayed 3 weeks after emergence with aqueous preparations of the active substances listed in the table below. The active substance concentrations in the spray broth were 1000, 500, 100 and 50 ppm respectively. The plant growth was evaluated 4 weeks after application in accordance with the following linear rating:

1 = strong inhibition (no growth from the time of application)

9 = no inhibition (growth as untreated controls)

The following results were obtained:

| Compound | Inhibition rating* 1000 ppm | 500 ppm | 100 ppm | 50 ppm |
|---|---|---|---|---|
| 1 | 2 | 2 | 2 | 2 |
| 3 | 1 | 2 | 4 | 6 |
| 13 | 1 | 2 | 4 | 3 |
| 2 | 2 | 3 | 4 | 3 |
| 6 | 1 | 1 | 1 | 2 |
| 7 | 3 | 3 | 3 | 3 |
| 14 | 4 | 6 | 6 | 6 |

*untreated plants: 9

Increase in the yield of soya

In a field of soya plants of the variety "Lee 68", 50 $m^2$ parcels were sprayed with aqueous preparations of the active substance 1 when the plants were in the 5- to 6-leaf stage. The rate of active substances was 500 g/ha. At harvesting time, it was observed that 90% of the untreated plants had been flattened by high winds (lodging), whereas all the plants in the treated parcels were upright. It is known that lodging is highly undesirable in soya (and other leguminosae and in cereal cultures) because it can result in substantial losses in yield. In this Example, treated parcels had higher yields compared with control parcels. The treated plants were also smaller and sturdier than the untreated ones. Strips with no growth remained between the rows of treated plants, whilst in the control parcels the entire area was overgrown. This fact indicates that the spaces between the rows of seeds can be narrowed by applying the growth regulator, compound 1, in addition to increased stability and an increase in yield per plant. This action results in further increases in yield through an increased population density.

Growth inhibition in chrysanthemums

In this Example, a chrysanthemum variety was used which, on account of its strong growth, can only be reared as pot plant in combination with growth inhibitors. Four weeks after the cuttings had been put into the pots, the plants were sprayed with aqueous preparations of the active substances listed in the following table. The rates of application were 500 and 250 ppm respectively. The growth in height of the plants was determined at the start of blossoming, approx. 4 weeks after the application.

The following results were obtained:

| Compound and concentration | | Growth inhibition (inhibition of new growth after application) |
|---|---|---|
| Control | (untreated) | 0% |
| Alar ® | 3000 ppm (standard) | 30% |
| 1 | 500 ppm | 70% |
| | 250 ppm | 60% |
| 12 | 500 ppm | 60% |
| | 250 ppm | 40% |
| 14 | 500 ppm | 60% |
| | 250 ppm | 50% |
| 40 | 500 ppm | 50% |
| | 250 ppm | 20% |
| 19 | 500 ppm | 70% |
| | 250 ppm | 60% |

Alar ® is the known growth inhibitor, succinic acid mono-N-dimethyl-hydrazide $(CH_3)_2N-NH-CO-NH_2-CH_2-COOH$.

Abscission effect

Segments of bean leaves of the variety "Tempo" were immersed in a solution with 20 and 10 ppm respectively of the compound 31 and left for 3 days under controlled conditions. Thereafter the number of abscissions (constrictions between pulvinus and petiole) was determined.

The following results were obtained:

| Treatment concentration of active substance 31 | Percentage of segments with constriction |
|---|---|
| Control (untreated) | 0% |
| 20 ppm | 70% |
| 10 ppm | 30% |

I claim:

1. A compound of the formula

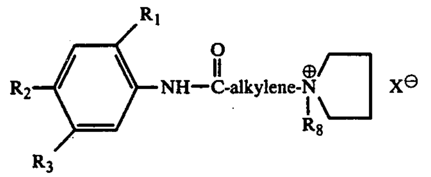

wherein $R_1$ is hydrogen, chlorine, methyl or trifluoromethyl,
$R_2$ is methyl, halogen or $C_1$-$C_4$ alkoxy,
$R_3$ is hydrogen, chlorine or trifluoromethyl,
"alkylene" has from 1 to 3 carbon atoms,
$R_8$ is $C_1$-$C_5$ alkyl, cyanomethyl, allyl, butenyl or propargyl, and
X is the anion of any non-phytotoxic acid.

2. A compound according to claim 1 in which
$R_1$ is chlorine, methyl or trifluoromethyl, and
$R_2$ is chlorine.

3. A compound according to claim 1 in which each of $R_1$ and $R_2$ is methyl or chlorine.

4. A compound according to claim 3 in which "alkylene" is methylene or ethylene, and
$R_8$ is $C_1$-$C_5$ alkyl, allyl, butenyl or propargyl.

5. A compound according to claim 4 in which "alkylene" is methylene.

6. The compound according to claim 5 of the formula

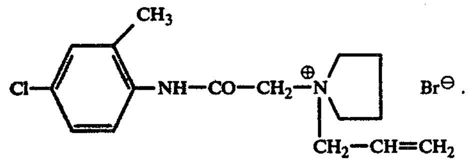

7. A compound according to claim 1 in which X is chlorine, bromine or iodine.

8. The compound according to claim 5 which is

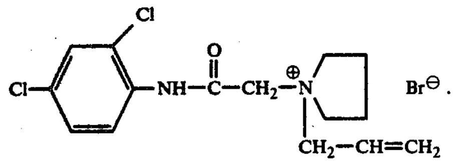

9. The compound according to claim 5 which is

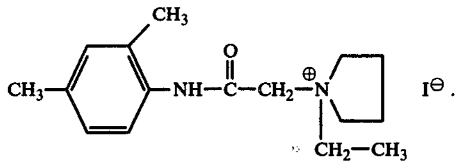

10. The compound according to claim 5 which is

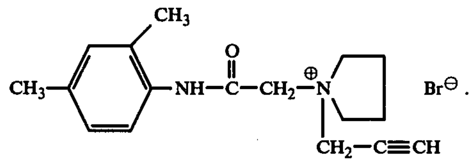

11. The compound according to claim 5 which is

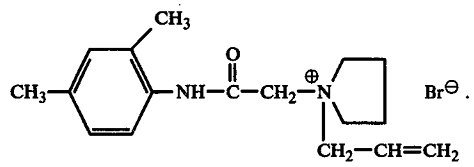

12. The compound according to claim 1 which is

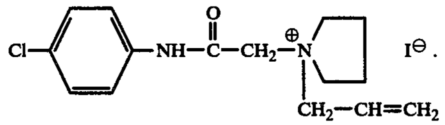

13. A compound of the formula

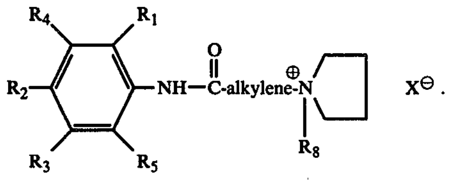

wherein each of $R_1$, $R_2$, $R_3$, $R_4$ and $R_5$ is hydrogen, methyl, fluorine, chlorine or trifluoromethyl,
"alkylene" has from 1 to 3 carbon atoms,
$R_8$ is $C_1$-$C_4$ alkyl, allyl, butenyl or propargyl, and
X is the anion of any non-phytoxic acid.

14. A compound according to claim 13 in which
$R_1$, $R_3$, $R_4$ and $R_5$ are hydrogen, and
$R_2$ is fluorine or chlorine.

15. A compound according to claim 13 in which $R_3$, $R_4$ and $R_5$ are hydrogen.

16. A compound according to claim 13 in which $R_1$, $R_4$ and $R_5$ are hydrogen.

17. A compound according to claim 13 in which $R_2$, $R_4$ and $R_5$ are hydrogen.

18. A compound according to claim 13 in which $R_2$, $R_3$ and $R_4$ are hydrogen.

19. A compound according to claim 13 in which $R_8$ is propyl, butyl, allyl, butenyl or propargyl.

20. A compound according to claim 19 in which $R_8$ is propyl.

21. A compound according to claim 19 in which $R_8$ is allyl.

22. A compound according to claim 21 in which "alkylene" is methylene.

23. A composition for inhibiting the growth of plants which comprises (1) a compound according to claim 1 and (2) a carrier.

24. A composition for inhibiting the growth of plants which comprises (1) a compound according to claim 5 and (2) a carrier.

25. A composition for inhibiting the growth of plants which comprises (1) a compound according to claim 13 and (2) a carrier.

26. A composition for inhibiting the growth of plants which comprises (1) a compound according to claim 22 and (2) a carrier.

27. A method for controlling the growth of plants which comprises applying thereto an effective amount of a compound according to claim 1.

28. A method for controlling the growth of plants which comprises applying thereto an effective amount of a compound according to claim 5.

29. A method for controlling the growth of plants which comprises applying thereto an effective amount of a compound according to claim 13.

30. A method for inhibiting the growth of plants which comprises applying thereto a growth inhibiting effective amount of a compound according to claim 1.

31. A method for inhibiting the growth of plants which comprises applying thereto a growth inhibiting effective amount of a compound according to claim 5.

32. A method for inhibiting the growth of plants which comprises applying thereto a growth inhibiting effective amount of a compound according to claim 13.

33. A method for inhibiting the growth of plants which comprises applying thereto a growth inhibiting effective amount of a compound according to claim 22.

34. A method for inhibiting the growth of ornamental plants which comprises applying to said plants, after emergence, a growth inhibiting effective amount of a compound according to claim 22.

35. A method for inhibiting the growth of ornamental plants which comprises applying thereto, after emergence, a growth inhibiting effective amount of the compound of claim 12.

36. A method for inhibiting the vegetative growth of dicotyledenous plants which comprises applying thereto a growth inhibiting effective amount of a compound according to claim 5.

37. A method for inhibiting the vegetative growth of dicotyledenous plants which comprises applying thereto a growth inhibiting effective amount of the compound of claim 8.

38. A method for inhibiting the vegetative growth of dicotyledenous plants which comprises applying thereto a growth inhibiting effective amount of the compound of claim 11.

39. A method for inhibiting the vegetative growth of soya plants which comprises applying thereto a growth inhibiting effective amount of a compound according to claim 5.

40. A method of inhibiting the vegetative growth of soya plants which comprises applying thereto a growth inhibiting effective amount of the compound of claim 6.

41. A method for inhibiting the vegetative growth of soya plants which comprises applying thereto a growth inhibiting effective amount of the compound of claim 9.

42. A method of inhibiting the vegetative growth of soya plants which comprises applying thereto a growth inhibiting effective amount of the compound of claim 10.

* * * * *

UNITED STATES PATENT AND TRADEMARK OFFICE
CERTIFICATE OF CORRECTION

PATENT NO. : 4,141,718

DATED : February 27, 1979

INVENTOR(S) : Henry Martin

It is certified that error appears in the above-identified patent and that said Letters Patent are hereby corrected as shown below:

At Column 62, in Claim 12 of the above-identified patent, the structural formula should appear as follows:

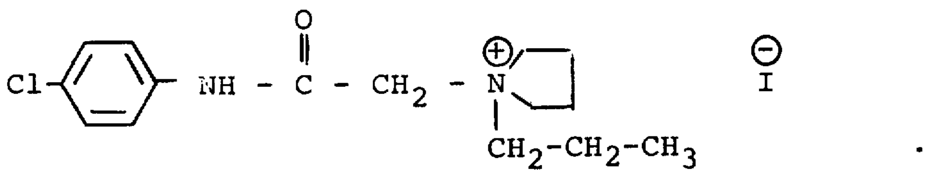

Signed and Sealed this

*Fifth* Day of *June 1979*

[SEAL]

*Attest:*

RUTH C. MASON
*Attesting Officer*

DONALD W. BANNER
*Commissioner of Patents and Trademarks*